(12) United States Patent
Pulukuri

(10) Patent No.: US 12,097,199 B2
(45) Date of Patent: Sep. 24, 2024

(54) ADMINISTRATION OF SUMO-ACTIVATING ENZYME INHIBITOR AND ANTI-CD20 ANTIBODIES

(71) Applicant: Takeda Pharmaceutical Company Limited, Osaka (JP)

(72) Inventor: Sai Murali Krishna Pulukuri, Sharon, MA (US)

(73) Assignee: Takeda Pharmaceutical Company Limited, Osaka (JP)

( * ) Notice: Subject to any disclaimer, the term of this patent is extended or adjusted under 35 U.S.C. 154(b) by 929 days.

(21) Appl. No.: 17/258,845

(22) PCT Filed: Jul. 8, 2019

(86) PCT No.: PCT/US2019/040838
§ 371 (c)(1),
(2) Date: Jan. 8, 2021

(87) PCT Pub. No.: WO2020/014139
PCT Pub. Date: Jan. 16, 2020

(65) Prior Publication Data
US 2021/0267972 A1 Sep. 2, 2021

Related U.S. Application Data

(60) Provisional application No. 62/695,630, filed on Jul. 9, 2018.

(51) Int. Cl.
*A61K 31/505* (2006.01)
*A61P 35/02* (2006.01)
*C07K 16/28* (2006.01)

(52) U.S. Cl.
CPC ............ *A61K 31/505* (2013.01); *A61P 35/02* (2018.01); *C07K 16/2887* (2013.01)

(58) Field of Classification Search
CPC .................................................. A61K 31/505
See application file for complete search history.

(56) References Cited

U.S. PATENT DOCUMENTS

| | | | |
|---|---|---|---|
| 5,736,137 A | 4/1998 | Anderson et al. | |
| 9,434,765 B2 | 9/2016 | Medina | |
| 9,683,003 B2* | 6/2017 | Duffey ................ | A61K 31/506 |
| 9,695,154 B2 | 7/2017 | Duffey et al. | |
| 9,962,386 B2* | 5/2018 | Duffey ................ | C07D 513/04 |
| 2010/0160177 A1 | 6/2010 | Merbl et al. | |
| 2012/0258927 A1 | 10/2012 | Langston et al. | |
| 2016/0009744 A1 | 1/2016 | Duffey et al. | |
| 2016/0333106 A1 | 11/2016 | Grillo-Lopez | |
| 2017/0174779 A1 | 6/2017 | Varghese et al. | |

FOREIGN PATENT DOCUMENTS

| | | |
|---|---|---|
| WO | WO 2004/035607 A2 | 4/2004 |
| WO | WO 2004/056312 A2 | 7/2004 |
| WO | WO 2005/044859 A2 | 5/2005 |
| WO | WO 2005/103081 A2 | 11/2005 |
| WO | WO 2010/043582 A1 | 4/2010 |
| WO | WO 2016/004136 A1 | 1/2016 |
| WO | WO-2020176772 A1 | 9/2020 |

OTHER PUBLICATIONS

Kyosuke, S., et al., "Molecular targeted therapy in myeloma and lymphoma," Journal of Okayama Medical Association 126(2):143-150, Okayama Medical Association, Japan (Aug. 2014).
English language translation of Office Action for Japanese Patent Application No. 2020-569041, dated May 26, 2023, 4 pages.
Armitage, James O. "A clinical evaluation of the International Lymphoma Study Group classification of non-Hodgkin's lymphoma." Blood 89(11): 3909-3918, Elsevier, Netherlands (1997).
Ballatore, Carlo, Virginia M-Y. Lee, and John Q. Trojanowski. "Tau-mediated neurodegeneration in Alzheimer's disease and related disorders." Nature reviews neuroscience 8(9): 663-672, Nature Publishing Group, England (2007).
Beham-Schmid, Christine. "Aggressive lymphoma 2016: revision of the WHO classification." memo-Magazine of European Medical Oncology 10(4): 248-254, (2017).
Berge, Stephen M., Lyle D. Bighley, and Donald C. Monkhouse. "Pharmaceutical salts." Journal of pharmaceutical sciences 66(1): 1-19, Elsevier, Netherlands (1977).
Berger, A.J., et al., abstract #3079 "Pharmacodynamic evaluation of the novel SUMOylation inhibitor TAK-981 in a mouse tumor model," Immunology: Experimental and Molecular therapeutics: Novel Antitumor Agents I 60:788, AACR Annual Meeting, United States (Mar. 2019), 1 page.
Bies, Juraj, Ján Markus, and Linda Wolff. "Covalent attachment of the SUMO-1 protein to the negative regulatory domain of the c-Myb transcription factor modifies its stability and transactivation capacity." Journal of Biological Chemistry 277(11): 8999-9009, (2002).
Chen, Shi-Feng, et al. "Ubc9 expression predicts chemoresistance in breast cancer." Chinese journal of cancer 30(9): 638-644 (2011).
Cragg, Mark S., and Martin J. Glennie. "Antibody specificity controls in vivo effector mechanisms of anti-CD20 reagents." Blood 103(7): 2738-2743, The American Society of Hematology (2004).
Cragg, Mark S., et al. "Complement-mediated lysis by anti-CD20 mAb correlates with segregation into lipid rafts." Blood, The Journal of the American Society of Hematology 101(3): 1045-1052, The American Society of Hematology (2003).

(Continued)

*Primary Examiner* — Golam M Shameem
(74) *Attorney, Agent, or Firm* — Sterne, Kessler, Goldstein & Fox P.L.L.C.

(57) ABSTRACT

The present disclosure provides methods, pharmaceutical compositions, and kits for treating cancer or autoimmune disease in patients in need thereof. The methods comprise administering to a patient in need a small ubiquitin-like modifier (SUMO) activating enzyme (SAE) inhibitor, such as [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxy-cyclopentyl]methyl sulfamate (Compound I-263a) or a pharmaceutically acceptable salt, in combination with one or more anti-CD20 antibodies. Also provided are medicaments for use in treating cancer or autoimmune disease.

21 Claims, 11 Drawing Sheets

(56) References Cited

OTHER PUBLICATIONS

Crowl, John T., and Daniel B. Stetson. "SUMO2 and SUMO3 redundantly prevent a noncanonical type I interferon response." Proceedings of the National Academy of Sciences 115(26): 6798-6803, National Academy of Sciences, United States (2018).
Decque, Adrien, et al. "Sumoylation coordinates the repression of inflammatory and anti-viral gene-expression programs during innate sensing." Nature immunology 17(2): 140-149, Nature Publishing, England (2016).
Desterro, Joana MP, Manuel S. Rodriguez, and Ronald T. Hay. "SUMO-1 modification of IκBα inhibits NF-κB activation." Molecular cell 2(2): 233-239, Elsevier, Netherlands (1998).
Dorval, Véronique, and Paul E. Fraser. "Small ubiquitin-like modifier (SUMO) modification of natively unfolded proteins tau and α-synuclein." Journal of Biological Chemistry 281(15): 9919-9924, The American Society for Biochemistry and Molecular Biology, Inc. (2006).
Driscoll, James J., et al. "The sumoylation pathway is dysregulated in multiple myeloma and is associated with adverse patient outcome." Blood, The Journal of the American Society of Hematology 115(14): 2827-2834, The American Society of Hematology (2010).
Ferlay, J., et al. "Cancer incidence and mortality patterns in Europe: Estimates for 40 countries and 25 major cancers in 2018." European journal of cancer 103: 356-387, Elsevier, Netherlands (2018).
Gill, Grace. "SUMO and ubiquitin in the nucleus: different functions, similar mechanisms?" Genes & development 18(17): 2046-2059, Cold Spring Harbor Laboratory Press, United States (2004).
Goodson, Michael L., et al. "Sumo-1 modification regulates the DNA binding activity of heat shock transcription factor 2, a promyelocytic leukemia nuclear body associated transcription factor." Journal of Biological Chemistry 276(21): 18513-18518, The American Society for Biochemistry and Molecular Biology, Inc. (2001).
Gribben, John G. "How I treat indolent lymphoma." Blood 109(11): 4617-4626, American Society of Hematology (2007).
Harris, Nancy Lee, et al. "The World Health Organization classification of neoplastic diseases of the hematopoietic and lymphoid tissues: report of the Clinical Advisory Committee meeting, Airlie House, Virginia, Nov. 1997." Annals of Oncology 10(12): 1419-1432, Elsevier, Netherlands (1999).
Hatton, B., et al., abstract #4136 "Direct intratumoral microdosing via the CIVO platform reveals anti-tumor immune responses induced by the SUMO inhibitor TAK-981," Immunology: Novel Immunomodulatory Agents 2 60:1065, AACR Annual Meeting, United States (Mar. 2019), 1 page.
Hay, Ronald T. "SUMO: a history of modification." Molecular cell 18 (1): 1-12, Elsevier, Netherlands (2005).
Hay, Ronald Thomas. "SUMO-specific proteases: a twist in the tail." Trends in cell biology 17(8): 370-376, Elsevier, Netherlands (2007).
He, Xingyue, et al. "Probing the roles of SUMOylation in cancer cell biology by using a selective SAE inhibitor." Nature chemical biology 13(11): 1164-1171, Nature Publishing (2017).
Hoellein, Alexander, et al. "Myc-induced SUMOylation is a therapeutic vulnerability for B-cell lymphoma." Blood, The Journal of the American Society of Hematology 124(13): 2081-2090, The American Society of Hematology (2014).
Johnson, Erica S., and Aseem A. Gupta. "An E3-like factor that promotes SUMO conjugation to the yeast septins." Cell 106(6): 735-744, (2001).
Kagey, Michael H., Tiffany A. Melhuish, and David Wotton. "The polycomb protein Pc2 is a SUMO E3." Cell 113(1): 127-137, (2003).
Kahl, Brad S., et al. "Rituximab extended schedule or Re-Treatment trial for low-tumor burden follicular lymphoma: eastern cooperative oncology group protocol E4402." Journal of Clinical Oncology 32(28): 3096-3102, American Society of Clincal Oncology (2014).
Kamitani, Tetsu, et al. "Characterization of a second member of the sentrin family of ubiquitin-like proteins." Journal of Biological Chemistry 273(18): 11349-11353, The American Society for Biochemistry and Molecular Biology, Inc. (1998).
Keating, Gillian M. "Rituximab." Drugs 70(11): 1445-1476, Springer Publishing, United States (2010).
Kerscher, Oliver, Rachael Felberbaum, and Mark Hochstrasser. "Modification of proteins by ubiquitin and ubiquitin-like proteins." Annu. Rev. Cell Dev. Biol. 22: 159-180, Annual Reviews, United States (2006).
Kessler, Jessica D., et al. "A SUMOylation-dependent transcriptional subprogram is required for Myc-driven tumorigenesis." Science 335(6066): 348-353, American Association for the Advancement of Science (2012).
Khattar, M., et al., abstract #3252 "TAK-981: A first in class SUMO inhibitor in Phase 1 trials that promotes dendritic cell activation, antigen-presentation and T cell priming," Immunology: Novel Immunomodulatory Agents I 60:837, AACR Annual Meeting, United States (Mar. 2019), 1 page.
Lee, Hye-Ra, et al. "Ability of the human cytomegalovirus IE1 protein to modulate sumoylation of PML correlates with its functional activities in transcriptional regulation and infectivity in cultured fibroblast cells." Journal of virology 78(12): 6527-6542, American Society for Microbiology (2004).
Liu, Bin, and Ke Shuai. "Summon SUMO to wrestle with inflammation." Molecular cell 35(6): 731-732, Elsevier, Netherlands (2009).
Mahajan, Rohit, et al. "A small ubiquitin-related polypeptide involved in targeting RanGAP1 to nuclear pore complex protein RanBP2." Cell 88(1): 97-107, Elsevier, Netherlands (1997).
Moschos, Stergios J., et al. "Expression analysis of Ubc9, the single small ubiquitin-like modifier (SUMO) E2 conjugating enzyme, in normal and malignant tissues." Human pathology 41(9): 1286-1298, Elsevier, Netherlands (2010).
Müller, Stefan, et al. "SUMO, ubiquitin's mysterious cousin." Nature reviews Molecular cell biology 2(3): 202-210, (2001).
Nakamura, A., et al., abstract #1523 "Inhibition of SUMOylation by TAK-981 induces antitumor innate immune responses by modulating macrophage and NK cell function through Type I IFN pathway activation," Immunology: Suppressive Myeloid Cells 60:390, AACR Annual Meeting, United States (Mar. 2019) 1 page.
National Comprehensive Cancer Network. "NCCN clinical practice guidelines in oncology (NCCN guidelines)." Central Nervous System Cancers Version 2: 19-21. National Comprehensive Cancer Network, May 6, 2019.
NCT03648372, A Study to Evaluate the Safety, Tolerability, Preliminary Efficacy and Pharmacokinetics (PK) of TAK-981 in Adult Participants With Advanced or Metastatic Solid Tumors or Relapsed/Refractory Hematologic Malignancies and in a Subset With Coronavirus Disease 2019 (COVID-19), ClinicalTrials.gov, accessed at https://clinicaltrials.gov/ct2/show/NCT03648372, accessed on Jan. 6, 2021, 7 pages.
Oflazoglu, Ezogelin, and Laurent P. Audoly. "Evolution of anti-CD20 monoclonal antibody therapeutics in oncology." MAbs. 2(1):14-19 Taylor & Francis, 2010.
Pichler, Andrea, et al. "The nucleoporin RanBP2 has SUMO1 E3 ligase activity." Cell 108(1): 109-120, Elsevier, Netherlands (2002).
Rodriguez, Manuel S., et al. "SUMO-1 modification activates the transcriptional response of p53." The EMBO journal 18(22): 6455-6461, Embo Press, Germany (1999).
Sachdev, Shrikesh, et al. "PIASy, a nuclear matrix-associated Sumo E3 ligase, represses LEF1 activity by sequestration into nuclear bodies." Genes & development 15(23): 3088-3103, Cold Spring Harbor Press, United States (2001).
Siegel RL, Miller KD, Jemal A. "Cancer statistics, 2018," CA Cancer J Clin. Jan. 2018;68(1):7-30, American Cancer Society (2018).
Steffan, Joan S., et al. "SUMO modification of Huntingtin and Huntington's disease pathology." Science 304(5667): 100-104, American Association for the Advancement of Science (2004).
Tatham, Michael H., et al. "Polymeric chains of SUMO-2 and SUMO-3 are conjugated to protein substrates by SAE1/SAE2 and

(56) References Cited

OTHER PUBLICATIONS

Ubc9." Journal of Biological Chemistry 276(38): 35368-35374, The American Society for Biochemistry and Molecular Biology, Inc. (2001).

Vaidya, R., and T. E. Witzig. "Prognostic factors for diffuse large B-cell lymphoma in the R (X) CHOP era." Annals of Oncology 25(11): 2124-2133, Elsevier, Netherlands (2014).

Wang, Jun, and Robert J. Schwartz. "Sumoylation and regulation of cardiac gene expression." Circulation Research 107(1): 19-29, Lippincott Williams & Wilkins, United States (2010).

International Search Report and Written Opinion for International Application No. PCT/US19/40838, United States Patent and Trademark Office, United States, mailed Sep. 4, 2019, 7 pages.

Corraliza-Gorjon et al., "New Strategies Using Antibody Combinations to Increase Cancer Treatment Effectiveness", Front. Immunol. Vol. 8 (1804) pp. 1-31 (2017).

Marshall et al. "Therapeutic Antibodies: What Have We Learnt from Targeting CD20 and Where Are We Going?" Frontiers in Immunology, vol. 8(1245) pp. 1-22, Antibody and Vaccine Group, Cancer Sciences Unit, Faculty of Medicine, University of Southampton, Southampton, United Kingdom, www.frontiersin.org (2017).

Mould et al., "Pharmacokinetics and Pharmacodynamics of Monoclonal Antibodies", BioDrugs, vol. 24, pp. 23-39 (2010).

Tallarida, Ronald J., "Quantitative Methods for Assessing Drug Synergism", Genes & Cancer, vol. 2(11) pp. 1003-1008 (2011).

Tyagi et al., "Use of chemical modification and chemical crosslinking to stabilize proteins (enzymes)", Biochemistry, vol. 63(3) pp. 395-407 (1998).

\* cited by examiner

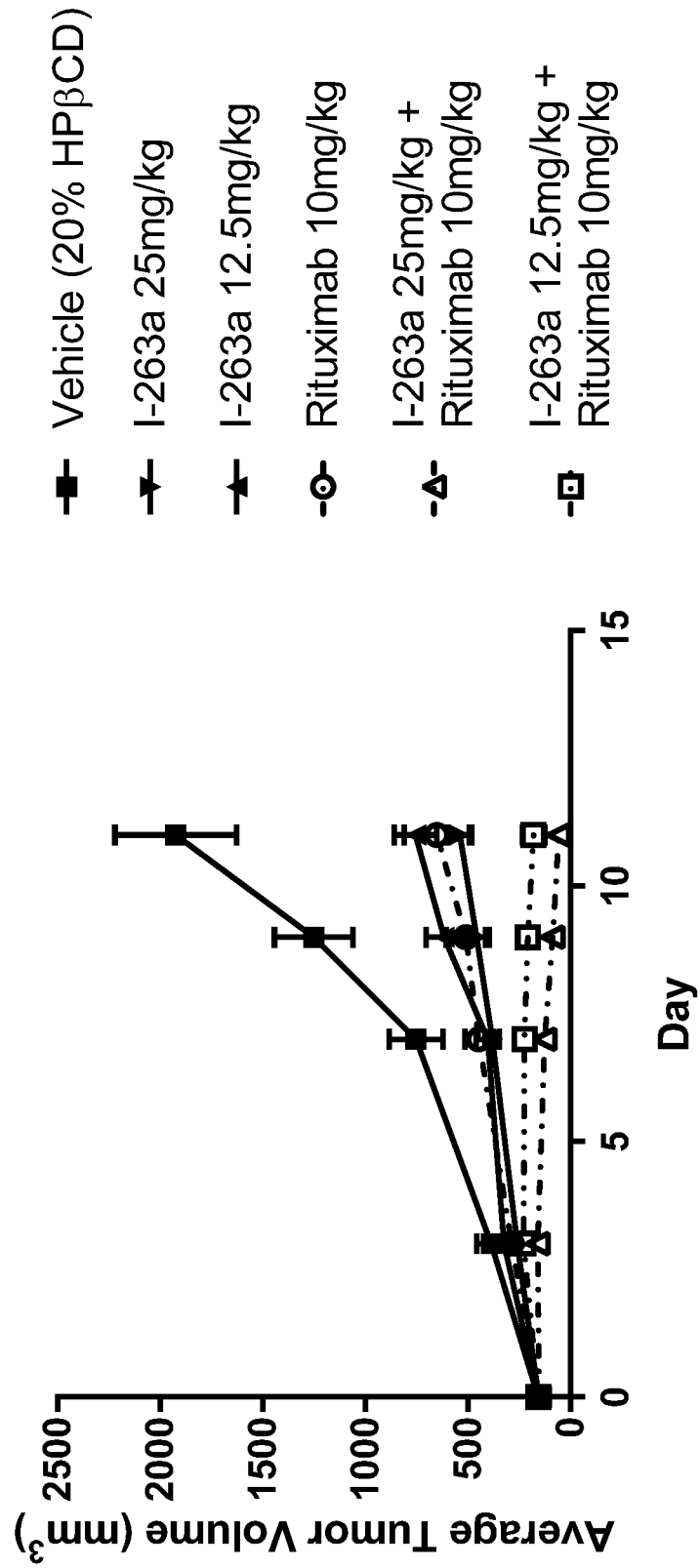

ADMINISTRATION OF SUMO-ACTIVATING ENZYME INHIBITOR AND ANTI-CD20 ANTIBODIES

CROSS REFERENCE TO RELATED APPLICATIONS

The present application is a national stage application, filed under 35 U.S.C. § 371, of International Patent Application No. PCT/US2019/040838, filed on Jul. 8, 2019, which claims priority to U.S. Provisional Application No. 62/695,630, filed on Jul. 9, 2018.

FIELD

The present disclosure relates to methods of treating cancer and autoimmune diseases. In particular, the present disclosure provides methods for treating various cancers and autoimmune diseases by administering a small ubiquitin-like modifier (SUMO) activating enzyme (SAE) inhibitor in combination with one or more anti-CD20 antibodies.

BACKGROUND

In 2012, there were an estimated 14 million cases of cancer diagnosed worldwide and about 8.2 million deaths. The global cancer burden is growing at an alarming pace; in 2030 alone, about 21.3 million new cancer cases and 13.1 million cancer deaths are expected to occur, simply due to the growth and aging of the population. Cancer is the second most common cause of death in the US, exceeded only by heart disease, accounting for nearly 1 of every 4 deaths. The National Cancer Institute estimates that approximately 14.5 million Americans with a history of cancer were alive in 2014. Some of these individuals were cancer free, while others still had evidence of cancer and may have been undergoing treatment. Although medical advances have improved cancer survival rates, there is a continuing need for new and more effective treatment.

Cancer treatments have mainly relied on the combination of surgery, radiotherapy, and/or cytotoxic chemotherapies. Within the last decade, however, targeted cancer therapies have opened a new era in the field of oncology. Targeted cancer therapies are drugs designed to interfere with specific molecules necessary for tumor growth and progression, and can include small molecules and larger chemical entities, such as monoclonal antibodies (mAbs).

Non-Hodgkin lymphoma (NHL) is among the most common cancers in the United States and Europe with more than 70,000 and 93,000 new cases diagnosed every year, respectively. Siegel R. L., et al., CA Cancer J. Clin. 68(1): 7-30 (2018); Ferlay J., et al., Eur. J. Cancer 103:356-87 (2018). NHL is a heterogeneous group of malignancies with varying clinical characteristics that are optimally managed through a range of different treatment modalities. The spectrum of NHL includes more indolent variants such as follicular and marginal zone lymphomas, to more aggressive subtypes such as diffuse large B-cell lymphoma (DLBCL). While systemic chemotherapy is a mainstay of treatment for most NHL variants, antitumor directed monoclonal antibodies have an important role in the treatment of this disease. Oflazoglu E., et al., MAbs 2(1): 14-9 (2010). Monoclonal antibodies such as rituximab, which targets the B-cell antigen CD20, are now part of the standard treatment regimens for many B-cell NHLs. Keating GM, Drugs 70(11): 1445-76 (2010). However, once NHL becomes refractory to standard chemotherapy and antibody-based therapies, the overall prognosis is poor, with limited long-term survival. Thus, novel and effective therapies are needed to address this high unmet medical need.

Indolent NHL (iNHL) represents 40% of all NHL subtypes, with follicular lymphoma occurring with the greatest frequency. Harris N. L., et al., Ann. Oncol. 10(12): 1419-32 (1999). iNHL presents with a broad spectrum of disease characteristics. Patients often experience a chronic relapsing and remitting disease course and are exposed to several successive treatment regimens, resulting eventually in death due to disease progression. In general, treatment is reserved for patients who develop significant symptoms or who are sufficiently high risk to merit early therapy. Gribben J. G., Blood 109(11):4617-26 (2007).

For patients with iNHL who initially respond (complete or partial response (PR) with a time to progression of at least 6 months) and then experience relapse after single-agent rituximab, retreatment with either rituximab alone or in combination with chemotherapy is frequently given. Gribben J. G., Blood 109(11):4617-26 (2007); Kahl B. S., et al., J. Clin. Oncol. 32(28):3096-102 (2014); NCCN Clinical Practice Guidelines in Oncology (NCCN Guidelines): B-Cell Lymphomas (Version 3.2019), National Comprehensive Cancer Network, May 6, 2019. Patients who become refractory to rituximab alone or in combination with chemotherapy have limited options for effective treatment.

Aggressive Non-Hodgkin Lymphoma (aNHL) accounts for approximately 30 to 40% of all NHL (Project TN-HsLC, Blood 89(11): 3909-18 (1997)) and DLBCL is the most common histological subtype. Beham-Schmid C., Aggressive lymphoma 2016: revision of the WHO classification, Memo 10(4):248-54 (2017). Combination chemotherapy with the addition of rituximab is standard of care for patients with newly diagnosed DLBCL. However, approximately 40% of patients with DLBCL relapse following initial immunochemotherapy. Vaidya R., et al., Ann. Oncol. 25(11): 2124-33 (2014). For eligible patients, salvage chemotherapy regimens followed by autologous stem cell transplantation is the standard of care. However, many patients are not eligible for transplantation due to age and other medical co-morbidities. While various salvage regimens comprising combination chemotherapy are available for relapsed/refractory disease, no standard salvage regimen exists currently. there remains an unmet need for NHL patients who have early relapses or who are not responsive to anti-CD20 treatment regimens.

Small ubiquitin-like modifier (SUMO) activating enzyme (SAE) inhibitors are examples of small molecules that can be used for targeted therapies. SUMO is a member of the ubiquitin-like protein (Ubl) family that covalently conjugate to cellular proteins in a manner similar to Ub-conjugation (Kerscher, O. et al., Annu Rev Cell Dev Biol. 22:159-80 (2006)). Mammalian cells express three major isoforms: SUMO1, SUMO2, and SUMO3. SUMO2 and SUMO3 share ~95% amino acid sequence homology but have ~45% sequence homology with SUMO1 (Kamitani, T., et al., J Biol Chem. 273(18):11349-53 (1998)). SUMO proteins can conjugate to a single lysine residue of a protein (monosumoylation) or to a second SUMO protein that is already conjugated to a protein forming a SUMO chain (polysumoylation). Only SUMO2/3 can form such chains because they possess internal consensus SUMO modification sites (Tatham, M. H., et al., J Biol Chem. 276(38):35368-74 (2001)). An additional isoform, SUMO4, is found in kidney, lymph node and spleen cells, but it is not known whether SUMO4 can conjugate to cellular proteins.

SUMO1, SUMO2 and SUMO3 are activated in an ATP-dependent manner by SAE (see, for example, U.S. Patent Application Publication No. 2010/0160177 A1 (FIG. 1B) and U.S. Pat. No. 9,434,765 B2 (FIG. 2)). SAE is a heterodimer that consists of SAE1 (SUMO-activating enzyme subunit 1) and SAE2 (UBA2). SAE, like other E1 activating enzymes, uses ATP to adenylate the C-terminal glycine residue of SUMO. In a second step, a thioester intermediate is then formed between the C-terminal glycine of SUMO and a cysteine residue in SAE2. Next, SUMO is transferred from the E1 to the cysteine residue of the SUMO conjugating enzyme (E2), UBC9. Unlike the Ub pathway that contains many E2 enzymes, Ubc9 is currently the only known conjugating enzyme for SUMO and functions with SUMO1, SUMO2, and SUMO3 proteins. SUMO proteins then conjugate to the target protein, either directly or in conjunction with an E3 ligase, through isopeptide bond formation with the epsilon amino group of a lysine side chain on a target protein. Several SUMO E3 ligases, including PIAS (protein inhibitor of activated signal transducer and activator of transcription protein) proteins and Ran-binding protein 2 (RanBP2), and polycomb 2 (Pc2), have been identified (Johnson, E. S., and Gupta, A. A, Cell. 106(6): 735-44 (2001); Pichler, A., et al., Cell. 108(1): 109-20 (2002); Kagey, M. H., et al., Cell. 113(1):127-37 (2003)). Once attached to cellular targets, SUMO modulates the function, subcellular localization, complex formation and/or stability of substrate proteins (Müller, S., et al., Nat Rev Mol Cell Biol. 2(3):202-10 (2001)). SUMO-conjugation is reversible through the action of de-sumoylating enzymes called SENPs (Hay, R. T., Trends Cell Biol. 17(8): 370-6 (2007)) and the SUMO proteins can then participate in additional conjugation cycles.

SAE-initiated SUMO-conjugation plays a major role in regulating diverse cellular processes, including cell cycle regulation, transcriptional regulation, cellular protein targeting, maintenance of genome integrity, chromosome segregation, and protein stability (Hay, R. T., Mol Cell. 18(1): 1-12 (2005); Gill, G., Genes Dev. 18(17):2046-59 (2004)). For example, SUMO-conjugation causes changes in the subcellular localization of RanGAP1 by targeting it to the nuclear pore complex (Mahajan, R., et al., Cell. 88(1):97-1070 (1997)). Sumoylation counteracts ubiquitination and subsequently blocks the degradation of IκB, thereby negatively regulating NF-κB activation (Desterro, J. M., et al., Mol Cell. 2(2):233-9 (1998)). Sumoylation has been reported to play an important role in transcription exhibiting both repressive and stimulatory effects. Many of the transcriptional nodes that are modulated play important roles in cancer. For example, sumoylation stimulates the transcriptional activities of transcription factors such as p53 and HSF2 (Rodriguez, M. S., et al., EMBO J. 18(22):6455-61 (1999); Goodson, M. L., et al., J Biol Chem. 276(21): 18513-8 (2001)). In contrast, SUMO-conjugation represses the transcriptional activities of transcription factors such as LEF (Sachdev, S., et al., Genes Dev. 15(23):3088-103 (2001)) and c-Myb (Bies, J., et al., J Biol Chem. 277(11): 8999-9009 (2002)). SUMOylation has also been shown to regulate the production of Type I interferons (Crowl, J. T. and Stetson, D. B. PNAS 115(26):6798-6803 (2018); Decque, A., et al., Nature Immunology 17(2): 140-149 (2016)). Thus, SUMO-conjugation controls gene expression and growth control pathways that are important for cancer cell survival.

Altered expression of SAE pathway components have been noted in a variety of cancer types: (Moschos, S. J., et al., Hum Pathol. 41(9): 1286-980 (2010)); including multiple myeloma (Driscoll, J. J., et al., Blood. 115(14):2827-34 (2010)); and breast cancer (Chen, S. F., et al., Chin J Cancer. 30(9):638-44 (2011)). In addition, preclinical studies indicate that Myc-driven cancers may be especially sensitive to SAE inhibition (Kessler, J. D., et al., Science. 335(6066): 348-53 (2012); Hoellein, A., et al., Blood. 124(13):2081-90 (2014)). Since SUMO-conjugation regulates essential cellular functions that contribute to the growth and survival of tumor cells, targeting SAE could represent an approach to treat proliferative disorders such as cancer. (He, X., et al., Nature Chemical Biology. 13: 1164-1171 (2017)). Thus, some cancers may be SAE-mediated disorders.

SAE inhibitors may also be applicable for the treatment of other diseases and conditions outside of oncology. For example, SUMO modifies proteins that play important roles in neurodegenerative diseases (Steffan, J. S., et al., Science. 304(5667): 100-4 (2004); Dorval, V., and Fraser, P. E., J Biol Chem. 281(15):9919-24 (2006); Ballatore, C., et al., Nat Rev Neurosci. 8(9):663-72(2007)). Sumoylation also has been reported to play an important role in pathogenic viral infection, inflammation and cardiac function (Lee, H. R., et al., J Virol. 78(12):6527-42 (2004); Liu, B., and Shuai, K., Mol Cell. 35(6): 731-2 (2009); Wang, J., and Schwartz, R. J., Circ Res.107(1): 19-29 (2010)).

In addition to small molecules, targeted therapies can include monoclonal antibodies. For example, among the many known monoclonal antibody targeted therapies are monoclonal antibodies to CD20 (e.g., rituximab/Rituxan® for treating lymphomas). Additional monoclonal antibody targeted therapies include, but are not limited to, monoclonal antibodies to CD52 (e.g., alemtuzumab/Campath®), VEGF (e.g., bevacizumab/Avastin®), HER2 (e.g., trastuzumab/Herceptin® for treating Her2+ breast and stomach cancers), and EGFR (e.g., cetuximab/Erbitux® for treating colorectal cancer).

New combinations of therapeutic agents that provide a beneficial effect in the treatment of cancers are desirable in order to prolong patient's lives while maintaining a high quality of life. New combinations may provide an increased benefit as compared to each of the agents alone. In particular, combined treatment regimens may be helpful for patients suffering from disease conditions including proliferative disorders, autoimmune diseases, inflammatory diseases, fibrotic diseases and kidney diseases, and could potentially even decrease the rate of relapse or overcome the resistance to a particular anticancer agent sometimes seen in these patients. This is especially true in the case where the cancers may be resistant or refractory to currently available therapeutic regimens.

Thus, there is a need for new cancer treatment regimens, including combination therapies.

SUMMARY

In one aspect, the present disclosure relates to methods of treating a disorder, wherein the disorder is cancer or autoimmune disease, comprising administering an SAE inhibitor and an anti-CD20 antibody in combination to a subject in need of such treatment.

In one aspect, the present disclosure relates to methods of treating a disorder, wherein the disorder is cancer or autoimmune disease, comprising administering to a patient in need of said treating a combination of [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, and an anti-CD20 antibody. Compound I-263a is also referred to herein as TAK-981.

In some embodiments, the anti-CD20 antibody is a Type I anti-CD20 antibody.

In some embodiments, the anti-CD20 antibody is a selected from the group consisting of HI47 IgG3 antibodies, 2C6 IgG1 antibodies, 2F2 IgG1 antibodies, and 2H7 IgG1 antibodies.

In some embodiments, the anti-CD20 antibody is a selected from the group consisting of ublituximab, ofatumumab, ocrelizumab, veltuzumab, obinutuzumab, AME-133v, ocaratuzumab, PRO131921, tositumomab, ibritumomab-tiuxetan, hA20, BLX-301, Reditux, PRO70769, and rituximab.

In some embodiments, the anti-CD20 antibody is rituximab.

In some embodiments, the anti-CD20 antibody is obinutuzumab.

In some embodiments, the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, is administered orally.

In some embodiments, the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, is administered intravenously. In some embodiments, the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, is administered subcutaneously.

In some embodiments, the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, is administered by intravenous infusion.

In some embodiments, the anti-CD20 antibody is administered intravenously.

In some embodiments, the anti-CD20 antibody is administered by intravenous infusion.

In some embodiments, the anti-CD20 antibody is administered by subcutaneous injection In some embodiments, the anti-CD20 antibody is administered subcutaneously.

In some embodiments, the disorder is cancer.

In some embodiments, the disorder is CD20 positive cancer.

In some embodiments, the disorder is hematological malignancy.

In some embodiments, the disorder is lymphoma or leukemia.

In some embodiments, the disorder is chronic lymphocytic leukemia or non-Hodgkin's lymphoma.

In some embodiments, the disorder is CD20 positive chronic lymphocytic leukemia or CD20 positive non-Hodgkin's lymphoma.

In some embodiments, the disorder is non-Hodgkin lymphoma. In some embodiments the subject suffers from relapsed or refractory non-Hodkins lymphoma. In some embodiments the disorder is follicular lymphoma (FL), marginal zone lymphoma (MZL), mantle cell lymphoma (MCL), Diffuse large B-cell lymphoma (DLBCL), or Burkitt lymphoma.

In some embodiments, the disorder is Rheumatoid Arthritis (RA), Granulomatosis with Polyangiitis (GPA), Microscopic Polyangiitis (MPA), pemphigus vulgaris (PV), thrombotic thrombocytopenia purpura (TTP), or Rasmussen encephalitis (RE).

In some embodiments, the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, is administered once every two weeks, once every week, twice a week, three times a week, or daily.

In some embodiments, the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, is administered twice a week.

In some embodiments, the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, is administered once every week.

In some embodiments, the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, is administered on days 1, 4, 8, and 11 of a 21 day cycle.

In some embodiments, the anti-CD20 antibody is administered once every two weeks, once every week, twice a week, three times a week, or daily.

In some embodiments, the anti-CD20 antibody is administered once every two weeks.

In some embodiments, the anti-CD20 antibody is administered once every week.

In some embodiments, the anti-CD20 antibody is administered once every four weeks.

In some embodiments, the anti-CD20 antibody is administered once every eight weeks.

In some embodiments, the anti-CD20 antibody is administered on Day 1 of a treatment cycle.

In some embodiments, the treatment cycle is 21 days or 28 days.

In some embodiments, the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, and the anti-CD20 antibody are administered simultaneously once every eight weeks, once every four weeks, once every two weeks, once every week, twice a week, three times a week, or daily.

In some embodiments, the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, and the anti-CD20 antibody are administered simultaneously on days 1, 4, 8, and 11 of a 21 day cycle In some embodiments, the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, is administered once every two weeks, once every week, twice a week, three times a week, daily, or on days 1, 4, 8, and 11 of a 21 day cycle; and the anti-CD20 antibody is separately administered once every eight weeks, once every four weeks, once every two weeks, once every week, twice a week, three times a week, or daily.

In one aspect, the present disclosure relates to a kit comprising a medicament for use in treating cancer or autoimmune disease in a subject in need of such treatment. The kit comprises a medicament comprising an SAE inhibitor, and instructions for administering the SAE inhibitor and the one or more anti-CD20 antibodies; or the kit comprises a medicament comprising the one or more anti-CD20 antibodies, and instructions for administering the one or more anti-CD20 antibodies and an SAE inhibitor. The kit can contain both a medicament comprising an SAE inhibitor and a medicament comprising one or more anti-CD20 antibodies, and instructions for administering the SAE inhibitor and the one or more anti-CD20 antibodies. The kit can also comprise one or more additional therapeutic agents.

In one aspect, the present disclosure relates to a medicament for use in treating cancer or autoimmune disease in a subject in need of such treatment. The medicament comprises an SAE inhibitor and one or more anti-CD20 antibodies. The medicament can also comprise one or more additional therapeutic agents.

BRIEF DESCRIPTION OF THE FIGURES

FIG. 5a shows a plot of tumor volume as a function of time during treatment period in a PHTX-166L primary xenograft model following administration of Compound I-263a and rituximab to mice.

DETAILED DESCRIPTION

Definitions and Abbreviations

Figure 1A:
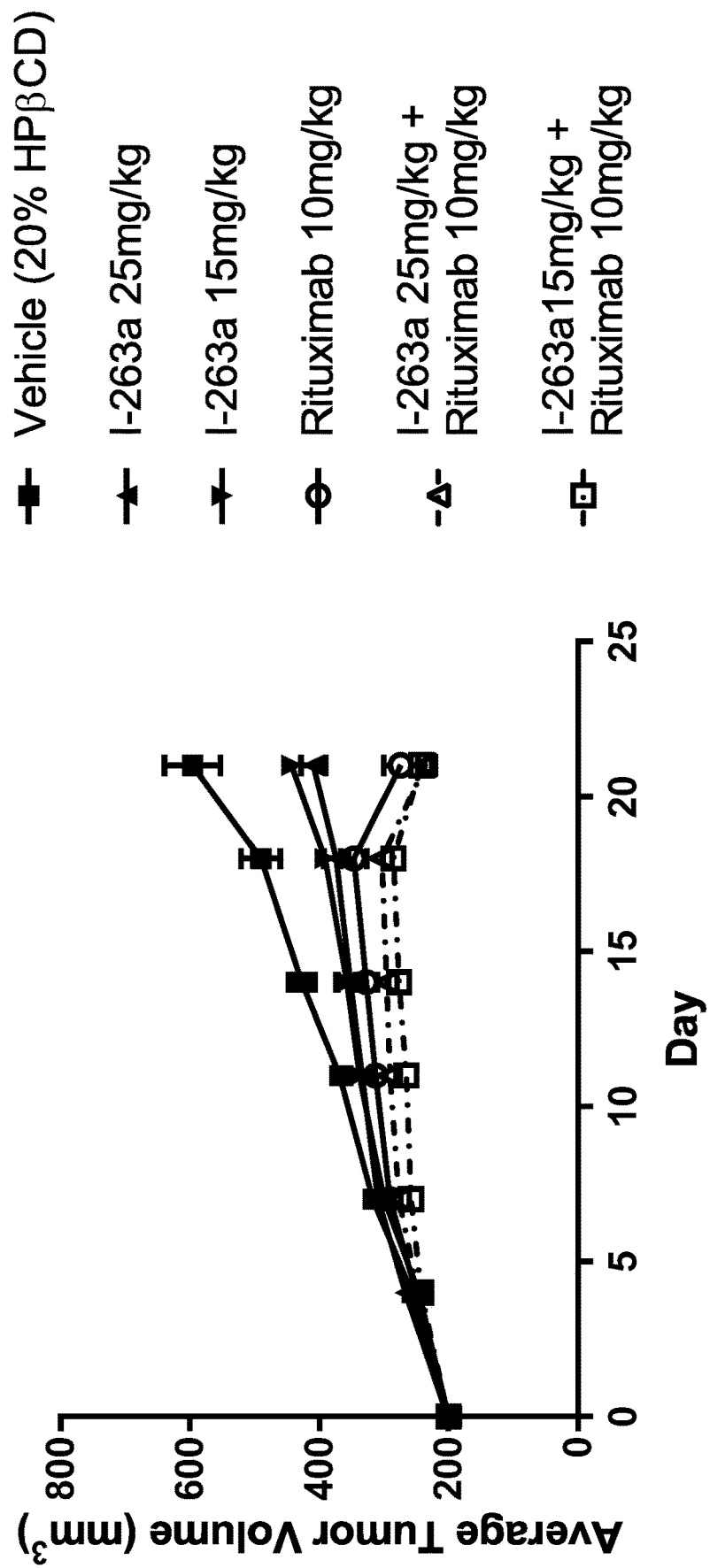
FIG. 1a shows a plot of tumor volume as a function of time during treatment period in a OCI-Ly 10 xenograft model following administration of Compound I-263a and rituximab to mice.

To facilitate an understanding of the present disclosure, a number of abbreviations, terms, and phrases are defined below.

AUC area under the plasma concentration versus time curve
BSA body surface area
CR complete response
MTD maximum tolerated dose
SUMO small ubiquitin-like modifier
SAE SUMO-activating enzyme
PR partial response
BIW twice weekly
QW once weekly
Q2W once every 2 weeks
QD once daily
QDx3 three times weekly
Q Every
NSCLC non-small cell lung cancer
SCLC small cell lung cancer
NHL Non-Hodgkin Lymphoma
aNHL aggressive Non-Hodgkin Lymphoma
iNHL indolent Non-Hodgkin Lymphoma
DLBCL Diffuse Large B-Cell Lymphomas Unless defined otherwise, all technical and scientific terms used herein have the same meaning as is commonly understood by one of skill in the art to which this disclosure belongs. All patents and publications referred to herein are incorporated by reference in their entirety.

As used herein, the term "cancer" refers to a cellular disorder characterized by uncontrolled or dysregulated cell proliferation, decreased cellular differentiation, inappropriate ability to invade surrounding tissue, and/or ability to establish new growth at ectopic sites. The term "cancer" includes solid tumors and non-solid tumors, such as, for example, hematological tumors. The term "cancer" encompasses diseases of skin, tissues, organs, bone, cartilage, blood, and vessels. The term "cancer" further encompasses primary and metastatic cancers.

As used herein, the term "autoimmune disease" refers to a disorder arising from an abnormal immune response to a normal body part. The term "autoimmune disease" encompasses disorders including, but not limited to, Rheumatoid Arthritis (RA), Granulomatosis with Polyangiitis (GPA) (Wegener's Granulomatosis), and Microscopic Polyangiitis (MPA).

The term "CD20" (also known as B lymphocyte CD20 antigen, MS4A1, B lymphocyte surface antigen B1, Bp35, Leukocyte surface antigen Leu-16) refers to any native CD20, unless otherwise indicated. The term "CD20" encompasses "full-length," unprocessed CD20 as well as any form of CD20 that results from processing within the cell. The term also encompasses naturally occurring variants of CD20, e.g., splice variants, allelic variants, and isoforms.

The term "antibody" means an immunoglobulin molecule that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the term "antibody" encompasses intact polyclonal antibodies, intact monoclonal antibodies, antibody fragments (such as Fab, Fab', F(ab')2, and Fv fragments), single chain Fv (scFv) mutants, multispecific antibodies such as bispecific antibodies generated from at least two intact antibodies, chimeric antibodies, humanized antibodies, human antibodies, fusion proteins comprising an antigen determination portion of an antibody, and any other modified immunoglobulin molecule comprising an antigen recognition site so long as the antibodies exhibit the desired biological activity. An antibody can be of any of the five major classes of immunoglobulins: IgA, IgD, IgE, IgG, and IgM, or subclasses (isotypes) thereof (e.g., IgG1, IgG2, IgG3, IgG4, IgA1 and IgA2), based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated to other molecules such as toxins, radioisotopes, etc.

A "blocking" antibody or an "antagonist" antibody is one which inhibits or reduces biological activity of the antigen it binds, such as, e.g., CD20. In a certain embodiment, blocking antibodies or antagonist antibodies substantially or completely inhibit the biological activity of the antigen. Desirably, the biological activity is reduced by 10%, 20%, 30%, 50%, 70%, 80%, 90%, 95%, or even 100%.

The term "anti-CD20 antibody" or "an antibody that binds to CD20" refers to an antibody that is capable of binding CD20 with sufficient affinity such that the antibody is useful as a diagnostic and/or therapeutic agent in targeting CD20. The extent of binding of an anti-CD20 antibody to an unrelated, non-CD20 protein is less than about 10% of the binding of the antibody to CD20 as measured, e.g., by a radioimmunoassay (RIA). In certain embodiments, an antibody that binds to CD20 has a dissociation constant (Kd) of ≤1 µM, ≤100 nM, ≤10 nM, ≤1 nM, or ≤0.1 nM.

Anti-CD20 antibodies can be organized into two categories: Type I and Type II anti-CD20 antibodies. See Cragg, M. S., et al., Blood 103, 2738-2743 (2004); Cragg, M. S., et al., Blood 101, 1045-1052 (2003). Examples of Type I anti-CD20 antibodies include, for example, rituximab, HI47 IgG3 (ECACC, hybridoma), 2C6 IgG1 (as disclosed in WO 2005/103081), 2F2 IgG1 (as disclosed and WO 2004/035607 and WO 2005/103081), and 2H7 IgG1 (as disclosed in WO 2004/056312). Examples of Type II anti-CD20 antibodies include, for example, humanized B-Ly1 antibody IgG1 (a chimeric humanized IgG1 antibody as disclosed in WO 2005/044859), 11B8 IgG1 (as disclosed in WO 2004/035607), and AT80 IgG1.

A "monoclonal antibody" refers to a homogeneous antibody population involved in the highly specific recognition and binding of a single antigenic determinant, or epitope. This is in contrast to polyclonal antibodies that typically include different antibodies directed against different antigenic determinants. The term "monoclonal antibody" encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal antibody" refers to such antibodies made in any number of manners including but not limited to by hybridoma, phage selection, recombinant expression, and transgenic animals.

The term "chimeric antibodies" refers to antibodies wherein the amino acid sequence of the immunoglobulin molecule is derived from two or more species. Typically, the variable region of both light and heavy chains corresponds to the variable region of antibodies derived from one species of mammals (e.g., mouse, rat, rabbit, etc.) with the desired specificity, affinity, and capability while the constant regions are homologous to the sequences in antibodies derived from another (usually human) to avoid eliciting an immune response in that species.

As used herein, the term "effective amount" or "therapeutically effective amount" refers to an amount of a compound, or combination of one or more compounds that, when administered (either sequentially or simultaneously) elicits the desired biological or medicinal response, e.g., either destroys the target cancer cells or slows or arrests the progression of the cancer in a patient. The therapeutically effective amount may vary depending upon the intended application (in vitro or in vivo), or the patient and disease condition being treated, e.g., the weight and age of the patient, the severity of the disease condition, the manner of administration and the like, which may readily be determined by one skilled in the art. The term also applies to a dose that will induce a particular response in target cells, e.g., reduction of platelet adhesion and/or cell migration. For example, in some embodiments, the "therapeutically effective amount" as used herein refers to the amount of [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, and the amount of an anti-CD20 antibody that, when administered separately or in combination, have a beneficial effect. In some embodiments, the combined effect is additive. In some embodiments, the combined effect is synergistic. Further, it will be recognized by one skilled in the art that in the case of combination therapy, the amount of [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof and/or the amount of the anti-CD20 antibody may be used in a "sub-therapeutic amount", i.e., less than the therapeutically effective amount of [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, or the anti-CD20 antibody alone.

In any form or composition, the administered dose(s) or the therapeutically effective (total) amount may be expressed as amount(s) of therapeutic substance(s) per patient as either based on (i) BSA, e.g., as mg/m$^2$, or (ii) amount, e.g., as mg.

The term "about" refers to approximately, in the region of, roughly, or around. When the term "about" is used in conjunction with a number or a numerical range, it means that the number or numerical range referred to is an approximation within experimental variability (or within statistical experimental error), and thus the number or numerical range may vary from, for example, between 1% and 15% of the stated number or numerical range. In general, the term "about" is used herein to modify a numerical value above and below the stated value by a variance of ±10%.

As used herein, "patient" generally means a mammal (e.g., human) who has been diagnosed with, exhibits symptoms of, or is otherwise believed to be afflicted with a disease, disorder, or condition (such as cancer).

As used herein, "body surface area" (BSA) is calculated using a standard nomogram, e.g., $$BSA(m^2) = \sqrt{\frac{Ht(\text{cm}) \times Wt(\text{kg})}{3600}}$$

or $$BSA = \sqrt{\frac{Ht(\text{in}) \times Wt(\text{lb})}{3131}}$$

The term "combination administration," "administered in combination," and "administering a combination" refers to administering of more than one pharmaceutically active ingredients (including, but not limited to, [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, and an anti-CD20 antibody as disclosed herein) to a patient. Combination administration may refer to simultaneous administration or may refer to sequential administration of the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, and an anti-CD20 antibody as disclosed herein.

The terms "simultaneous" and "simultaneously" refer to the administration of the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, and an anti-CD20 antibody as disclosed herein, to a patient at the same time, or at two different time points that are separated by no more than 2 hours. The simultaneous administration of the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, and an anti-CD20 antibody may be in a single dosage form or in separate dosage forms.

The terms "sequential" and "sequentially" refer to the administration of the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, and an anti-CD20 antibody as disclosed herein, to a patient at two different time points that are separated by more than 2 hours, e.g., about 3 hours, about 4 hours, about 5 hours, about 8 hours, about 12 hours, 1 day, 2 days, 3 days, 4 days, 5 days, 6 days, 7 days or even longer.

The term "intermission" refers to a period that is subsequent to the administration of one or more particular pharmaceutically active ingredients to a patient in an intermittent regimen. Intermission refers to a rest period wherein a particular pharmaceutically active ingredient is not administered for at least one day.

The term "synergistic effect" refers to a situation where the combination of two or more agents produces a greater effect than the sum of the effects of each of the individual agents. The term encompasses not only a reduction in symptoms of the disorder to be treated, but also an improved side effect profile, improved tolerability, improved patient compliance, improved efficacy, or any other improved clinical outcome.

As used herein, the illustrative terms "include", "such as", "for example" and the like (and variations thereof, e.g., "includes" and "including", "examples"), unless otherwise specified, are intended to be non-limiting. That is, unless explicitly stated otherwise, such terms are intended to imply "but not limited to", e.g., "including" means including but not limited to.

Unless otherwise stated, structures depicted herein are meant to include chemical entities which differ only in the presence of one or more isotopically enriched atoms. For example, chemical entities having the present structure except for the replacement of a hydrogen atom by a deuterium or tritium, or the replacement of a carbon atom by a $^{13}$C- or $^{14}$C-enriched carbon are within the scope of the invention.

Unless stereochemical configuration is denoted, structures depicted herein are meant to include all stereochemical forms of the structure, i.e., the R and S configurations for each asymmetric center. Therefore, unless otherwise indicated, single stereochemical isomers as well as enantiomeric, racemic and diastereomeric mixtures of the present chemical entities are within the scope of the invention. When a stereochemical configuration is denoted for a compound, the diastereoisomeric or enantiomeric excess of the compound is at least 99.0%, 99.5%, 99.6%, 99.7%, 99.8% or 99.9%.

SAE Inhibitor

The present disclosure provides a combination treatment for patients with cancer or autoimmune disease. The combination treatment includes, inter alia, administering to a subject in need thereof a therapeutically effective amount of at least one SAE inhibitor.

In some embodiments, the SAE inhibitor is [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate, or a pharmaceutically acceptable salt thereof, having the following structure:

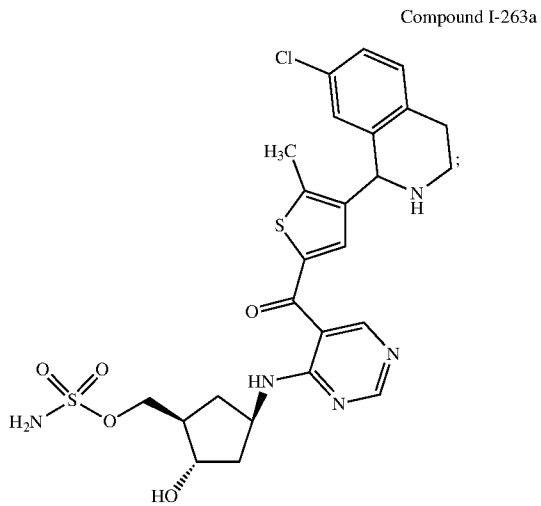 [SMILES: Cc1sc(C(=O)c2cncnc2N[C@@H]2C[C@H](COS(N)(=O)=O)[C@@H](O)C2)cc1C1NCCc2ccc(Cl)cc21]

Compound I-263a

[(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate is also referred to herein as Compound I-263a.

In some embodiments, the SAE inhibitor is [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate, or a pharmaceutically acceptable salt thereof.

In some embodiments, the SAE inhibitor is [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate, or Compound I-263a.

SAE inhibitors, as disclosed herein, are described, for example, in US 2016/0009744 and U.S. Pat. No. 9,695,154. They may be prepared by methods known to one skilled in the art and/or according to the methods described in US 2016/0009744 and U.S. Pat. No. 9,695,154, which is hereby incorporated by reference in its entirety. Central to the mechanism of action of useful SAE inhibitors, such as Compound I-263a, in combinations and methods of the present disclosure is production of type 1 IFNs and induction of an innate immune response with activation of both natural killer (NK) cells and macrophages. Biochemical assays have demonstrated that Compound I-263a is a mechanism-based inhibitor of SUMO-activating enzyme that potently inhibits enzyme activity by forming a covalent adduct with SUMO. Strong selectivity for SUMO-activating enzyme was observed over the other closely related ubiquitin-activating enzymes ubiquitin-activating enzyme, Nedd8-activating enzyme, and autophagy related 7 enzyme. Selective and potent inhibition of SUMO-activating enzyme and SUMOylation by Compound I-263a has been demonstrated in cultured mouse and human tumor cell lines and the antiproliferative activity of Compound I-263a has been determined in a panel of 7 mouse hematologic and solid tumor cell lines.

In some embodiments, the SAE inhibitor is [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a crystalline form thereof.

In some embodiments, the SAE inhibitor or a pharmaceutical salt thereof is crystalline form 1 of [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a), as described in U.S. published application number US 2016/0009744.

In some embodiments, the SAE inhibitor or a pharmaceutical salt thereof is crystalline form 2 of [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a), as described in U.S. published application number US 2016/0009744.

In some embodiments, the SAE inhibitor or a pharmaceutical salt thereof is crystalline form 3 of [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a), described in U.S. published application number US 2016/0009744.

Anti-CD20 Antibodies

The present disclosure provides a combination treatment that includes, inter alia, administering to a subject in need thereof a therapeutically effective amount of at least one anti-CD20 antibody (e.g., rituximab).

CD20 is a hydrophobic transmembrane phosphoprotein that is expressed predominantly in pre-B cells and mature peripheral B cells in humans and mice. In humans, CD20 is also strongly and homogeneously expressed in most mature B-cell malignancies, including, for example, most non-Hodgkin's B-cell lymphomas (NHL) and B-type Chronic Lymphocytic Leukemia's (B-CLL). The CD20 antigen is not expressed on haematopoietic stem cells or on plasmocytes.

In some embodiments, the anti-CD20 antibody is a Type I anti-CD20 antibody or a Type II anti-CD20 antibody. In some embodiments, the anti-CD20 antibody is a Type I anti-CD20 antibody.

In some embodiments, the anti-CD20 antibody is selected from the group consisting of HI47 IgG3 antibodies, 2C6 IgG1 antibodies, 2F2 IgG1 antibodies, 2H7 IgG1 antibodies, and rituximab. In some embodiments, the anti-CD20 antibody is rituximab.

Rituximab is a genetically engineered chimeric murine/human monoclonal antibody directed against the CD20 antigen. In some embodiments, rituximab is the antibody called "C2B8" in U.S. Pat. No. 5,736,137. In some embodiments, the amino acid sequence of rituximab antibody and exemplary methods for its production via recombinant expression in Chinese Hamster Ovary (CHO) cells are disclosed in U.S. Pat. No. 5,736,137. Rituximab was initially approved by the FDA in 1997 for treating non-Hodgkin's lymphoma. In some embodiments, rituximab is commercially available as Rituxan® or MabThera®. In some embodiments, rituximab is a biosimilar or an interchangeable product, such as Truxima®, Rixathon®, Mabion CD20, ABP 798, PF-05280586, RGB-03, or SAIT101.

Additional anti-CD20 antibodies include, for example, ublituximab (TG-1101), ofatumumab (HuMax; Intracel), ocrelizumab (Roche), veltuzumab, obinutuzumab (GA101), AME-133v (Applied Molecular Evolution), ocaratuzumab (Mentrik Biotech), PRO131921, tositumomab, ibritumomab-tiuxetan, hA20 (Immunomedics, Inc.), BLX-301 (Biolex Therapeutics), Reditux (Dr. Reddy's Laboratories), and PRO70769 (described in WO2004/056312).

In some embodiments, the anti-CD20 antibody used in the methods (and kits) described herein is rituximab or an anti-CD20 antibody that binds to the same epitope as rituximab. In some embodiments, the anti-CD20 antibody is rituximab. In some embodiments, the anti-CD20 antibody is ocrelizumab.

Methods of Treating Cancer or Autoimmune Disease

In some embodiments, the present disclosure relates to a method of treating a disorder which is cancer or autoimmune disease in a patient by administering to a patient in need of said treating a combination of an SAE inhibitor or pharmaceutically acceptable salt thereof and one or more anti-CD20 antibodies.

In some embodiments, the present disclosure relates to a method of treating a disorder which is cancer or autoimmune disease by administering to a patient in need of said treating a combination of an SAE inhibitor and an anti-CD20 antibody.

In some embodiments, the present disclosure relates to the use of an SAE inhibitor in combination with an anti-CD20 antibody for the treatment of a disorder which is cancer or autoimmune disease in a patient.

In some embodiments, the present disclosure relates to a composition comprising an SAE inhibitor for use in treating a disorder which is cancer or autoimmune disease in a patient, wherein the patient is also treated with an anti-CD20 antibody. In some aspects, the disclosure relates to a composition comprising an SAE inhibitor for use in treating a disorder which is cancer or autoimmune disease in a patient, wherein the SAE inhibitor is in combination with the anti-CD20 antibody. In some embodiments, the SAE inhibitor can be administered simultaneously or sequentially with the anti-CD20 antibody.

In some embodiments, the present disclosure relates to methods of treating a disorder which is cancer or autoimmune disease comprising administering to a patient in need of such treatment, a therapeutically effective amount of a combination of an SAE inhibitor and an anti-CD20 antibody.

In some embodiments, the present disclosure relates to a method of treating a disorder which is cancer or autoimmune disease by administering to a patient a combination of Compound I-263a, or pharmaceutically acceptable salt thereof, and an anti-CD20 antibody.

In another aspect, the present disclosure relates to the use of Compound I-263a, or a pharmaceutically acceptable salt thereof, in combination with an anti-CD20 antibody for the treatment of a disorder which is cancer or autoimmune disease.

In some embodiments, the methods of treating a disorder which is cancer or autoimmune disease, as described herein, can include a combination of an SAE inhibitor, an anti-CD20 antibody, and one or more additional therapeutic agents. In some embodiments, the one or more additional therapeutic agents can be chemotherapeutic agents. In some embodiments, the one or more additional therapeutic agents can include, but are not limited to, fludarabine, cyclophosphamide, doxorubicin, vincristine, methotrexate anthracycline-based chemotherapeutic agents, prednisone, methylprednisolone, glucocorticoids, Ibritumomab tiuxetan, acetaminophen, antihistamines, and combinations thereof. In another embodiment, the anti-CD20 antibody is coadministered with human hyaluronidase.

In some embodiments, the disorder is cancer. In some embodiments, the disorder is a CD20-positive cancer.

In some embodiments, the cancer is a solid tumor. Non-limiting examples of solid tumors include pancreatic cancer; bladder cancer, including invasive bladder cancer; colorectal cancer; thyroid cancer; gastric cancer; breast cancer, including metastatic breast cancer; prostate cancer, including androgen-dependent and androgen-independent prostate cancer; renal cancer, including, e.g., metastatic renal cell carcinoma; liver cancer including e.g. hepatocellular carcinoma and intrahepatic bile duct cancer; lung and bronchus cancer including non-small cell lung cancer (NSCLC), squamous lung cancer, brochioloalveolar carcinoma (BAC), adenocarcinoma of the lung, and small cell lung cancer (SCLC); ovarian cancer including, e.g., progressive epithelial and primary peritoneal cancer; cervical cancer; uterine cancer including e.g. uterine corpus and uterine cervix; endometrial cancer; esophageal cancer; head and neck cancer, including, e.g., squamous cell carcinoma of the head and neck, nasopharyngeal caner, oral cavity and pharynx; melanoma; neuroendocrine cancer, including metastatic neuroendocrine tumors; brain cancer, including, e.g., glioma/glioblastoma, anaplastic oligodendroglioma, adult glioblastoma multiforme, adult anaplastic astrocytoma, and medulloblastoma; neuroendocrine cancer, including metastatic neuroendocrine tumors; bone cancer; gastro-esophageal junction cancer, and soft tissue sarcoma.

In some embodiments, the cancer is a hematological cancer. Non-limiting examples of hematologic malignancies include acute myeloid leukemia (AML); chronic myelogenous leukemia (CML), including accelerated CML and CML blast phase (CML-BP); acute lymphoblastic leukemia (ALL); chronic lymphocytic leukemia (CLL); Hodgkin's lymphoma (HL); non-Hodgkin's lymphoma (NHL), including B-cell lymphoma, T-cell lymphoma, follicular lymphoma (FL), marginal zone lymphoma (MZL), mantle cell lymphoma (MCL), diffuse large B-cell lymphoma (DLBCL), and Burkitt lymphoma; multiple myeloma (MM); amyloidosis; Waldenstrom's macroglobulinemia; myelodysplastic syndromes (MDS), including refractory anemia (RA), refractory anemia with ringed sideroblasts (RARS), (refractory anemia with excess blasts (RAEB), and RAEB in transformation (RAEB-T); and myeloproliferative syndromes. In some embodiments, the cancer is chronic lymphocytic leukemia (CLL), Hodgkin's lymphoma, or non-Hodgkin's lymphoma including follicular lymphoma (FL), marginal zone lymphoma (MZL), mantle cell lymphoma (MCL), Diffuse large B-cell lymphoma (DLBCL) and Burkitt lymphoma.

In some embodiments, the cancer is chronic lymphocytic leukemia. In some embodiments, the cancer is CD-20 positive chronic lymphocytic leukemia.

In some embodiments, the cancer is non-Hodgkin's lymphoma, including follicular lymphoma (FL), marginal zone lymphoma (MZL), mantle cell lymphoma (MCL), Diffuse large B-cell lymphoma (DLBCL), and Burkitt lymphoma. In some embodiments, the cancer is B-cell lymphoma. In some embodiments, the cancer is CD-20 positive non-Hodgkin's lymphoma. In some embodiments, the cancer is CD20-positive aggressive non-Hodgkin lymphoma. In some embodiments, the cancer is CD20-positive indolent non-Hodgkin lymphoma. In some embodiments, the cancer is relapsed or refractory non-Hodgkin lymphoma. In some embodiments, the cancer is relapsed or refractory CD20-positive aggressive non-Hodgkin lymphoma. In some embodiments, the cancer is relapsed or refractory CD20-positive indolent non-Hodgkin lymphoma.

In some embodiments, the cancer is relapsed. In some embodiments, relapsed cancer is cancer which has returned after a period of time in which no cancer could be detected.

In some embodiments, the cancer is refractory. In some embodiments, refractory cancer does not respond to cancer treatment; it is also known as resistant cancer. In some embodiments, the cancer is resistant to rituximab. In some embodiments, the cancer does not respond to the treatment of rituximab. In some embodiments, the cancer is rituximab-resistant recurrent cancer. In some embodiments, the patient has become refractory to a rituximab-containing regimen. In some embodiments, the tumor is unresectable. In some embodiments, an unresectable tumor is unable to be removed by surgery. In some embodiments, the cancer has not been previously treated. In some embodiments, the cancer is locally advanced. In some embodiments, "locally advanced" refers to cancer that is somewhat extensive but still confined to one area. In some instances, "locally advanced" may refer to a small tumor that hasn't spread but has invaded nearby organs or tissues that make it difficult to remove with surgery alone. In some embodiments, the cancer is metastatic. In some embodiments, metastatic cancer is a cancer that has spread from the part of the body where it started (the primary site) to other parts of the body.

In some embodiments, the patient has relapsed or refractory CD20-positive non-Hodgkin lymphoma. In some embodiments, the patient has both CD20-positive non-Hodgkin lymphoma and relapsed or refractory non-Hodgkin lymphoma.

In some embodiments, the patient has relapsed or refractory CD20-positive aggressive non-Hodgkin lymphoma. In some embodiments, the patient has relapsed or refractory CD20-positive aggressive non-Hodgkin lymphoma and has progressed on at least one prior treatment regimen.

In some embodiments, the patient has relapsed or refractory CD20-positive indolent non-Hodgkin lymphoma. In some embodiments, the patient has relapsed or refractory CD20-positive indolent non-Hodgkin lymphoma and has progressed on at least two prior treatment regimens. In some embodiments, the patient has relapsed or refractory CD20-positive indolent non-Hodgkin lymphoma and is refractory to any anti-CD20 monoclonal antibody. In some embodiments, the patient has relapsed or refractory CD20-positive indolent non-Hodgkin lymphoma and has progressed on at least two prior treatment regimens and is refractory to any anti-CD20 monoclonal antibody.

In some embodiments, the disorder is an SAE-mediated disorder other than cancer.

In some embodiments, the disorder is an autoimmune disease.

In some embodiments, the disorder is Rheumatoid Arthritis (RA).

In some embodiments, the disorder is Granulomatosis with Polyangiitis (GPA) (Wegener's Granulomatosis), Microscopic Polyangiitis (MPA), pemphigus vulgaris (PV), thrombotic thrombocytopenia purpura (TTP), or Rasmussen encephalitis (RE).

Medicament

In some embodiments, the present disclosure relates to a medicament for use in treating a disorder which is cancer or autoimmune disease in a patient in need of such treatment. The medicament comprises an SAE inhibitor and an anti-CD20 antibody, and is in single dosage form or in separate dosage forms.

In some embodiments, the medicaments, as described herein, can include a combination of an SAE inhibitor, an anti-CD20 antibody, and optionally one or more additional therapeutic agents.

In some embodiments, the present disclosure relates to the use of an SAE inhibitor in the manufacture of a medicament for treating a disorder which is cancer or autoimmune disease, wherein the SAE inhibitor is administered with an anti-CD20 antibody, and wherein the medicament is in single dosage form or in separate dosage forms. In some embodiments, the SAE inhibitor is administered with an anti-CD20 antibody and one or more additional therapeutic agents.

In some embodiments, the present disclosure relates to the use of an SAE inhibitor for the manufacture of a medicament in treating a disorder which is cancer or autoimmune disease in a patient, wherein the patient is also treated with an anti-CD20 antibody, and optionally one or more additional therapeutic agents. In some embodiments, the SAE inhibitor may be administered simultaneously or sequentially with the anti-CD20 antibody. In some aspects, the present disclosure relates to the use of an SAE inhibitor for the manufacture of a medicament in treating a disorder which is cancer or autoimmune disease in a patient, wherein the SAE inhibitor is in combination with an anti-CD20 antibody, and optionally one or more additional therapeutic agents. In some embodiments, the SAE inhibitor is in the same composition as the anti-CD20 antibody. In some embodiments, the SAE inhibitor is in a separate composition as the anti-CD20 antibody. In some embodiments, the SAE inhibitor is in the same composition as one or more additional therapeutic agents. In some embodiments, the SAE inhibitor is in the same composition as the anti-CD20 antibody, and optionally one or more additional therapeutic agents. In some embodiments, the SAE inhibitor is in a separate composition as one or more additional therapeutic agents. In some embodiments, the SAE inhibitor is in a separate composition as the anti-CD20 antibody, and optionally one or more additional therapeutic agents.

In another aspect, the present disclosure relates to the use of Compound I-263a, or a pharmaceutically acceptable salt thereof in combination with an anti-CD20 antibody in the manufacture of a medicament for use in treating a disorder which is cancer or autoimmune disease. In some embodiments, the present disclosure relates to the use of Compound I-263a, or a pharmaceutically acceptable salt thereof in combination with an anti-CD20 antibody, and optionally one or more additional therapeutic agents in the manufacture of a medicament for use in treating a disorder which is cancer or autoimmune disease.

In another aspect, the present disclosure relates to the use of Compound I-263a, or a pharmaceutically acceptable salt thereof, in the manufacture of a medicament for treating a disorder which is cancer or autoimmune disease, wherein Compound I-263a or a pharmaceutically acceptable salt thereof is administered with an anti-CD20 antibody, and optionally one or more additional therapeutic agents.

In some embodiments, the one or more additional therapeutic agents can be chemotherapeutic agents. In some embodiments, the one or more additional therapeutic agents can include, but are not limited to, fludarabine, cyclophosphamide, doxorubicin, vincristine, methotrexate anthracycline-based chemotherapeutic agents, prednisone, methylprednisolone, glucocorticoids, Ibritumomab tiuxetan, acetaminophen, antihistamines, and combinations thereof. In another embodiment, the anti-CD20 antibody is coadministered with human hyaluronidase.

Administration of the Combination

Compound I-263a or a pharmaceutically acceptable salt thereof, may be administered in combination with the anti-CD20 antibody, and optionally one or more additional therapeutic agents, in a single dosage form or as a separate dosage forms. In some embodiments, when administered as a separate dosage form, the anti-CD20 antibody may be administered prior to, at the same time as, or following administration of I-263a or a pharmaceutically acceptable salt thereof. In some embodiments, when administered as a separate dosage form, one or more doses of I-263a or a pharmaceutically acceptable salt thereof, may be administered prior to the anti-CD20 antibody. In some embodiments, the anti-CD20 antibody is administered prior to the administration of Compound I-263a or a pharmaceutically acceptable salt thereof. As used herein, the administration in "combination" of Compound I-263a or a pharmaceutically acceptable salt thereof, an anti-CD20 antibody, and optionally one or more additional therapeutic agents refers not only to simultaneous or sequential administration of the agents, but also to the administration of the agents during a single treatment cycle, as understood by one skilled in the art. When Compound I-263a or a pharmaceutically acceptable salt thereof is administered in combination with the anti-CD20 antibody, and optionally one or more additional therapeutic agents, a therapeutically effective amount of the combination is administered.

The SAE inhibitor may be administered by any method known to one skilled in the art. For example, in some embodiments, the SAE inhibitor may be administered in the form of a pharmaceutical composition of the SAE inhibitor and a pharmaceutically acceptable carrier, such as those described herein. In some embodiments, the pharmaceutical composition is suitable for oral administration. In some embodiments, the pharmaceutical composition is a tablet or a capsule that is suitable for oral administration. In some other embodiments, the pharmaceutical composition is a liquid dosage form suitable for oral administration. In some embodiments, the pharmaceutical composition is suitable for intravenous administration. In some embodiments, the pharmaceutical composition is suitable for subcutaneous administration. In some embodiments, these compositions optionally further comprise one or more additional therapeutic agents.

The anti-CD20 antibody may be administered by any method known to one skilled in the art. In some embodiments, the anti-CD20 antibody is administered intravenously (IV). In some embodiments, the anti-CD20 antibody is administered subcutaneously (SC). In some embodiments, the anti-CD20 antibody is administered orally. For example, the anti-CD20 antibody may be administered in the form of a second composition, in some embodiments, a pharmaceutical composition of the anti-CD20 antibody and a pharmaceutically acceptable carrier, such as those described herein. In some aspects, the pharmaceutical composition is suitable for oral administration. In some embodiments, the pharmaceutical composition is a tablet or a capsule that is suitable for oral administration. In some other embodiments, the pharmaceutical composition is a liquid dosage form suitable for oral administration. In some embodiments, these compositions optionally further comprise one or more additional therapeutic agents.

The amounts or suitable doses of the methods of this disclosure depends upon a number of factors, including the nature of the severity of the condition to be treated, the particular inhibitor, the route of administration and the age, weight, general health, and response of the individual patient. In some embodiments, the suitable dose level is one that achieves a therapeutic response as measured by tumor regression, or other standard measures of disease progression, progression free survival or overall survival. In some embodiments, the suitable dose level is one that achieves this therapeutic response and also minimizes any side effects associated with the administration of the therapeutic agent. The suitable dose levels may be ones that prolong the therapeutic response and/or prolong life.

It will be understood that a suitable dose of the SAE inhibitor, the anti-CD20 antibody, and optionally one or more additional therapeutic agents may be taken at any time of the day or night. In some embodiments, a suitable dose of each agent is taken in the morning. In some other embodiments, a suitable dose of each agent is taken in the evening. In some embodiments, a suitable dose of each of the agents is taken both in the morning and the evening. It will be understood that a suitable dose of each agent may be taken with or without food. In some embodiments a suitable dose of an agent is taken with a meal. In some embodiments a suitable dose of an agent is taken while fasting.

In some embodiments, Compound I-263a or a pharmaceutically acceptable salt thereof is administered on a daily schedule. In some embodiments, Compound I-263a or a pharmaceutically acceptable salt thereof is administered every other day. In some embodiments, Compound I-263a or a pharmaceutically acceptable salt thereof is administered once every three days. In some embodiments, Compound I-263a or a pharmaceutically acceptable salt thereof is administered on a twice-weekly schedule. In some embodiments, Compound I-263a or a pharmaceutically acceptable salt thereof is administered on a three times a week schedule. In some embodiments, Compound I-263a or a pharmaceutically acceptable salt thereof is administered on a weekly schedule. In some embodiments, Compound I-263a or a pharmaceutically acceptable salt thereof is administered on a once every two weeks schedule.

In some embodiments, Compound I-263a or a pharmaceutically acceptable salt thereof is administered at least 3 times on alternate days within a 7-day cycle. In some embodiments, Compound I-263a or a pharmaceutically acceptable salt thereof is administered on day 1 and day 4 of a 7-day cycle. In some embodiments, Compound I-263a or a pharmaceutically acceptable salt thereof is administered on consecutive days in a 7-day cycle followed by an intermission. In some embodiments, Compound I-263a or a pharmaceutically acceptable salt thereof is administered for 2 consecutive days followed by an intermission of 5 consecutive days for at least one 7-day cycle. In some embodiments, Compound I-263a or a pharmaceutically acceptable salt thereof is administered for 3 consecutive days followed by an intermission of 4 consecutive days for at least one 7-day cycle. In some embodiments, Compound I-263a or a pharmaceutically acceptable salt thereof is administered for 4 consecutive days followed by an intermission of 3 consecutive days for at least one 7-day cycle. In some embodiments, Compound I-263a or a pharmaceutically acceptable salt thereof is administered for 5 consecutive days followed by an intermission of 2 consecutive days for at least one 7-day cycle. In some embodiments, there will be periods of rest between one or more of the 7-day treatment cycles. In some embodiments, there will be a 7-day rest between one or more of the 7-day treatment cycles.

The present description contemplates administration of the drug for one or more treatment cycles, for example, 1, 2, 3, 4, 5, 6, or more, treatment cycles. In some embodiments, a treatment cycle is about 7 days to about 56 days, or more. In some embodiments, a treatment cycle is 7 days, 14 days, 21 days, 28 days, 35 days, 42 days, 49 days, or 56 days. In some embodiments, a treatment cycle is 21 days or 28 days. In some embodiments, there will be periods of rest within or between one or more of the treatment cycles. For example, in some embodiments, there will be a period of rest at the end of the treatment cycle. In some embodiments, there will be a period of rest between the second and third treatment cycle but not the first and second treatment cycle. In another embodiment, there might be a period of rest between the first and second treatment cycle but not the second and third treatment cycle. Dosing schedules include, for example, administering the SAE inhibitor once during a treatment schedule, e.g., on day 1 of a 21 day cycle, twice during a treatment cycle, e.g., on days 1 and 15 of a 21 day cycle or on days 1 and 15 of a 28 day cycle, three times during a treatment cycle, e.g., on days 1, 8 and 15 of a 21 day cycle or on days 1, 8 and 15 of a 28 day cycle, and four times during a treatment cycle, e.g., on days 1, 4, 8, and 11 of a 21 day cycle or on days 1, 4, 8, and 11 of a 28 day cycle. Other dosage schedules are encompassed by the present invention.

In some embodiments, Compound I-263a or a pharmaceutically acceptable salt thereof is administered within a 21-day cycle. In some embodiments, Compound I-263a or a pharmaceutically acceptable salt thereof is administered at least two times within a 21-day cycle. In some embodiments, Compound I-263a or a pharmaceutically acceptable salt thereof is administered on day 1 within a 21-day cycle. In some embodiments, Compound I-263a or a pharmaceutically acceptable salt thereof is administered on day 8 within a 21-day cycle. In some embodiments, Compound I-263a or a pharmaceutically acceptable salt thereof is administered on days 1 and 8 within a 21-day cycle.

In some embodiments, Compound I-263a or a pharmaceutically acceptable salt thereof is administered for a duration of 1 year or less. In some embodiments, Compound I-263a or a pharmaceutically acceptable salt thereof is administered for a duration of 1 year or more.

In some embodiments, the amount of Compound I-263a or a pharmaceutically acceptable salt thereof that is administered on each day of dosing is about 0.5 mg to about 200 mg. In some embodiments, the amount of Compound I-263a or a pharmaceutically acceptable salt thereof that is administered on each day of dosing is about 0.5 mg to about 100 mg. In some embodiments, the amount of Compound I-263a or a pharmaceutically acceptable salt thereof that is administered on each day of dosing is about 0.5 mg to about 50 mg. In some embodiments, the amount of Compound I-263a or a pharmaceutically acceptable salt thereof that is administered on each day of dosing is about 0.5 mg to about 10 mg. In some embodiments, the amount of Compound I-263a or a pharmaceutically acceptable salt thereof that is administered on each day of dosing is about 0.5 mg to about mg. In some embodiments, the amount of Compound I-263a or a pharmaceutically acceptable salt thereof that is administered on each day of dosing is about 1 mg to about 3 mg. In some embodiments, the amount of Compound I-263a or a pharmaceutically acceptable salt thereof that is administered on each day of dosing is about 2 mg to about 5 mg. In some embodiments, the amount of Compound I-263a or a pharmaceutically acceptable salt thereof that is administered on each day of dosing is about 5 mg to about mg. In some embodiments, the amount of Compound I-263a or a pharmaceutically acceptable salt thereof that is administered on each day of dosing is about 5 mg to about mg. In some embodiments, the amount of Compound I-263a or a pharmaceutically acceptable salt thereof that is administered on each day of dosing is about 10 mg to about mg. In some embodiments, the amount of Compound I-263a or a pharmaceutically acceptable salt thereof that is administered on each day of dosing is about 15 mg to about 25 mg. In some embodiments, the amount of Compound I-263a or a pharmaceutically acceptable salt thereof that is administered on each day of dosing is between about 20 mg to about 30 mg. In some embodiments, the amount of Compound I-263a or a pharmaceutically acceptable salt thereof that is administered on each day of dosing is between about 25 mg to about 35 mg. In some embodiments, the amount of Compound I-263a or a pharmaceutically acceptable salt thereof that is administered on each day of dosing is between about 30 mg to about 40 mg. In some embodiments, the amount of Compound I-263a or a pharmaceutically acceptable salt thereof that is administered on each day of dosing is between about 35 mg to about 45 mg. In some embodiments, the amount of Compound I-263a or a pharmaceutically acceptable salt thereof that is administered on each day of dosing is between about 40 mg to about 50 mg. In some embodiments, the amount of Compound I-263a or a pharmaceutically acceptable salt thereof that is administered on each day of dosing is between about 55 mg to about 65 mg. In some embodiments, the amount of Compound I-263a or a pharmaceutically acceptable salt thereof that is administered on each day of dosing is between about 50 mg to about 100 mg. In some embodiments, the amount of Compound I-263a or a pharmaceutically acceptable salt thereof that is administered on each day of dosing is between about 90 mg to about 150 mg. In some embodiments, the amount of Compound I-263a or a pharmaceutically acceptable salt thereof that is administered on each day of dosing is between about 140 mg to about 200 mg. In some embodiments, the amount of Compound I-263a or a pharmaceutically acceptable salt thereof that is administered on each day of dosing is about 0.5 mg. In some embodiments, the amount of Compound I-263a or a pharmaceutically acceptable salt thereof that is administered on each day of dosing is about 1 mg. In some embodiments, the amount of Compound I-263a or a pharmaceutically acceptable salt thereof that is administered on each day of dosing is about 2 mg. In some embodiments, the amount of Compound I-263a or a pharmaceutically acceptable salt thereof that is administered on each day of dosing is about 3 mg. In some embodiments, the amount of Compound I-263a or a pharmaceutically acceptable salt thereof that is administered on each day of dosing is about 4 mg. In some embodiments, the amount of Compound I-263a or a pharmaceutically acceptable salt thereof that is administered on each day of dosing is about 6 mg. In some embodiments, the amount of Compound I-263a or a pharmaceutically acceptable salt thereof that is administered on each day of dosing is about 8 mg. In some embodiments, the amount of Compound I-263a or a pharmaceutically acceptable salt thereof that is administered on each day of dosing is about 10 mg. In some embodiments, the amount of Compound I-263a or a pharmaceutically acceptable salt thereof that is administered on each day of dosing is about 12 mg. All dosing amounts refer to the amount of Compound I-263a administered, and do not include the weight amount of any pharmaceutically acceptable salt.

In some embodiments, the amount of Compound I-263a or a pharmaceutically acceptable salt thereof that is administered on each day of dosing is about 1 mg. In some embodiments, the amount of Compound I-263a or a pharmaceutically acceptable salt thereof that is administered on each day of dosing is about 3 mg. In some embodiments, the amount of Compound I-263a or a pharmaceutically acceptable salt thereof that is administered on each day of dosing is about 6 mg. In some embodiments, the amount of Compound I-263a or a pharmaceutically acceptable salt thereof that is administered on each day of dosing is about 10 mg. In some embodiments, the amount of Compound I-263a or a pharmaceutically acceptable salt thereof that is administered on each day of dosing is about 15 mg. In some embodiments, the amount of Compound I-263a or a pharmaceutically acceptable salt thereof that is administered on each day of dosing is about 25 mg. In some embodiments, the amount of Compound I-263a or a pharmaceutically acceptable salt thereof that is administered on each day of dosing is about 40 mg. In some embodiments, the amount of Compound I-263a or a pharmaceutically acceptable salt thereof that is administered on each day of dosing is about 60 mg. In some embodiments, the amount of Compound I-263a or a pharmaceutically acceptable salt thereof that is administered on each day of dosing is about 90 mg. In some embodiments, the amount of Compound I-263a or a pharmaceutically acceptable salt thereof that is administered on each day of dosing is about 120 mg. In some embodiments, the amount of Compound I-263a or a pharmaceutically acceptable salt thereof that is administered on each day of dosing is about 160 mg.

In some embodiments, the anti-CD20 antibody is administered on a daily schedule. In some embodiments, the anti-CD20 antibody is administered every other day. In some embodiments, the anti-CD20 antibody is administered once every three days. In some embodiments, the anti-CD20 antibody is administered on a twice-weekly schedule. In some embodiments, the anti-CD20 antibody is administered on a three times a week schedule. In some embodiments, the anti-CD20 antibody is administered on a weekly schedule. In some embodiments, the anti-CD20 antibody is administered on a once every two weeks schedule. In some embodiments, the anti-CD20 antibody is administered on a once every three weeks schedule. In some embodiments, the anti-CD20 antibody is administered on a once every four weeks schedule.

In some embodiments, the anti-CD20 antibody is administered at least 3 times on alternate days within a 7-day cycle. In some embodiments, the anti-CD20 antibody is administered on day 1 and day 4 of a 7-day cycle. In some embodiments, the anti-CD20 antibody is administered on consecutive days in a 7-day cycle followed by an intermission. In some embodiments, the anti-CD20 antibody is administered for 2 consecutive days followed by an intermission of 5 consecutive days for at least one 7-day cycle. In some embodiments, the anti-CD20 antibody is administered for 3 consecutive days followed by an intermission of 4 consecutive days for at least one 7-day cycle. In some embodiments, the anti-CD20 antibody is administered for 4 consecutive days followed by an intermission of 3 consecutive days for at least one 7-day cycle. In some embodiments, the anti-CD20 antibody is administered for 5 consecutive days followed by an intermission of 2 consecutive days for at least one 7-day cycle.

In some embodiments, the anti-CD20 antibody is administered within a 21-day cycle. In some embodiments, the anti-CD20 antibody is administered on Day 1 within a 21-day cycle.

In some embodiments, the anti-CD20 antibody is administered weekly for three doses. In some embodiments, the anti-CD20 antibody is administered weekly for three doses and then administered on Day 1 within at least one 21-day cycle.

In some embodiments, the anti-CD20 antibody is administered by subcutaneous injection. In some embodiments, the anti-CD20 antibody is administered by intravenous infusion followed by one or more subsequent subcutaneous injections. In some embodiments, the intravenous infusion and one or more subsequent subcutaneous injections are administered according to the dosing schedules and methods disclosed herein.

In some embodiments, the amount of the anti-CD20 antibody that is administered on each day of dosing is about 0.5 mg/m$^2$ to about 2000 mg/m$^2$. In some embodiments, the amount of the anti-CD20 antibody that is administered on each day of dosing is about 0.5 mg/m$^2$ to about 1500 mg/m$^2$. In some embodiments, the amount of the anti-CD20 antibody that is administered on each day of dosing is about 0.5 mg/m$^2$ to about 1000 mg/m$^2$. In some embodiments, the amount of the anti-CD20 antibody that is administered on each day of dosing is about 1 mg/m$^2$ to about 1000 mg/m$^2$. In some embodiments, the amount of the anti-CD20 antibody that is administered on each day of dosing is about 10 mg/m$^2$ to about 1000 mg/m$^2$. In some embodiments, the amount of the anti-CD20 antibody that is administered on each day of dosing is about 50 mg/m$^2$ to about 1000 mg/m$^2$. In some embodiments, the amount of the anti-CD20 antibody that is administered on each day of dosing is about 100 mg/m$^2$ to about 1000 mg/m$^2$. In some embodiments, the amount of the anti-CD20 antibody that is administered on each day of dosing is about 150 mg/m$^2$ to about 1000 mg/m$^2$. In some embodiments, the amount of the anti-CD20 antibody that is administered on each day of dosing is between about 200 mg/m$^2$ to about 1000 mg/m$^2$. In some embodiments, the amount of the anti-CD20 antibody that is administered on each day of dosing is between about 250 mg/m$^2$ to about 1000 mg/m$^2$. In some embodiments, the amount of the anti-CD20 antibody that is administered on each day of dosing is about 200 mg/m$^2$. In some embodiments, the amount of the anti-CD20 antibody that is administered on each day of dosing is about 250 mg/m$^2$. In some embodiments, the amount of the anti-CD20 antibody that is administered on each day of dosing is about 300 mg/m$^2$. In some embodiments, the amount of the anti-CD20 antibody that is administered on each day of dosing is about 325 mg/m$^2$. In some embodiments, the amount of the anti-CD20 antibody that is administered on each day of dosing is about 350 mg/m$^2$. In some embodiments, the amount of the anti-CD20 antibody that is administered on each day of dosing is about 375 mg/m$^2$. In some embodiments, the amount of the anti-CD20 antibody that is administered on each day of dosing is about 400 mg/m$^2$. In some embodiments, the amount of the anti-CD20 antibody that is administered on each day of dosing is about 450 mg/m$^2$. In some embodiments, the amount of the anti-CD20 antibody that is administered on each day of dosing is about 500 mg/m$^2$. In some embodiments, the amount of the anti-CD20 antibody that is administered on each day of dosing is about 600 mg/m$^2$. In some embodiments, the amount of the anti-CD20 antibody that is administered on each day of dosing is about 700 mg/m$^2$. In some embodiments, the amount of the anti-CD20 antibody that is administered on each day of dosing is about 800 mg/m$^2$. In some embodiments, the amount of the anti-CD20 antibody that is administered on each day of dosing is about 900 mg/m$^2$. In some embodiments, the amount of the anti-CD20 antibody that is administered on each day of dosing is about 1000 mg/m$^2$. In some embodiments, the amount of the anti-CD20 antibody that is administered on each day of dosing is about 1500 mg/m$^2$. In some embodiments, the amount of the anti-CD20 antibody that is administered on each day of dosing is about 2000 mg/m$^2$. All dosing amounts refer to the amount of the anti-CD20 antibody administered, and do not include the weight amount of any pharmaceutically acceptable salt.

In some embodiments, the amount of the anti-CD20 antibody that is administered on each day of dosing is about 375 mg/m$^2$.

In some embodiments, the anti-CD20 antibody is rituximab, or a pharmaceutically acceptable salt thereof. In some embodiments, the amount of rituximab or a pharmaceutically acceptable salt thereof that is administered on each day of dosing is about 0.5 mg/m$^2$ to about 2000 mg/m$^2$. In some embodiments, the amount of rituximab or a pharmaceutically acceptable salt thereof that is administered on each day of dosing is about 0.5 mg/m$^2$ to about 1500 mg/m$^2$. In some embodiments, the amount of rituximab or a pharmaceutically acceptable salt thereof that is administered on each day of dosing is about 0.5 mg/m$^2$ to about 1000 mg/m$^2$. In some embodiments, the amount of rituximab or a pharmaceutically acceptable salt thereof that is administered on each day of dosing is about 1 mg/m$^2$ to about 1000 mg/m$^2$. In some embodiments, the amount of rituximab or a pharmaceutically acceptable salt thereof that is administered on each day of dosing is about 10 mg/m$^2$ to about 1000 mg/m$^2$. In some embodiments, the amount of rituximab or a pharmaceutically acceptable salt thereof that is administered on each day of dosing is about 50 mg/m$^2$ to about 1000 mg/m$^2$. In some embodiments, the amount of rituximab or a pharmaceutically acceptable salt thereof that is administered on each day of dosing is about 100 mg/m$^2$ to about 1000 mg/m$^2$. In some embodiments, the amount of rituximab or a pharmaceutically acceptable salt thereof that is administered on each day of dosing is about 150 mg/m² to about 1000 mg/m². In some embodiments, the amount of rituximab or a pharmaceutically acceptable salt thereof that is administered on each day of dosing is about 200 mg/m² to about 1000 mg/m². In some embodiments, the amount of rituximab or a pharmaceutically acceptable salt thereof that is administered on each day of dosing is about 250 mg/m² to about 1000 mg/m². In some embodiments, the amount of rituximab or a pharmaceutically acceptable salt thereof that is administered on each day of dosing is about 200 mg/m². In some embodiments, the amount of rituximab or a pharmaceutically acceptable salt thereof that is administered on each day of dosing is about 250 mg/m². In some embodiments, the amount of rituximab or a pharmaceutically acceptable salt thereof that is administered on each day of dosing is about 300 mg/m². In some embodiments, the amount of rituximab or a pharmaceutically acceptable salt thereof that is administered on each day of dosing is about 325 mg/m². In some embodiments, the amount of rituximab or a pharmaceutically acceptable salt thereof that is administered on each day of dosing is about 350 mg/m². In some embodiments, the amount of rituximab or a pharmaceutically acceptable salt thereof that is administered on each day of dosing is about 375 mg/m². In some embodiments, the amount of rituximab or a pharmaceutically acceptable salt thereof that is administered on each day of dosing is about 400 mg/m². In some embodiments, the amount of rituximab or a pharmaceutically acceptable salt thereof that is administered on each day of dosing is about 450 mg/m². In some embodiments, the amount of rituximab or a pharmaceutically acceptable salt thereof that is administered on each day of dosing is about 500 mg/m². In some embodiments, the amount of rituximab or a pharmaceutically acceptable salt thereof that is administered on each day of dosing is about 600 mg/m². In some embodiments, the amount of rituximab or a pharmaceutically acceptable salt thereof that is administered on each day of dosing is about 700 mg/m². In some embodiments, the amount of rituximab or a pharmaceutically acceptable salt thereof that is administered on each day of dosing is about 800 mg/m². In some embodiments, the amount of rituximab or a pharmaceutically acceptable salt thereof that is administered on each day of dosing is about 900 mg/m². In some embodiments, the amount of rituximab or a pharmaceutically acceptable salt thereof that is administered on each day of dosing is about 1000 mg/m². In some embodiments, the amount of rituximab or a pharmaceutically acceptable salt thereof that is administered on each day of dosing is about 1400 mg/m². In some embodiments, the amount of rituximab or a pharmaceutically acceptable salt thereof that is administered on each day of dosing is about 1500 mg/m². In some embodiments, the amount of rituximab or a pharmaceutically acceptable salt thereof that is administered on each day of dosing is about 1600 mg/m². In some embodiments, the amount of rituximab or a pharmaceutically acceptable salt thereof that is administered on each day of dosing is about 2000 mg/m². All dosing amounts refer to the amount of rituximab or a pharmaceutically acceptable salt thereof administered, and do not include the weight amount of any pharmaceutically acceptable salt.

In some embodiments, the amount of rituximab or a pharmaceutically acceptable salt thereof that is administered on each day of dosing is about 375 mg/m².

In some embodiments, the administration of rituximab is in accordance with its prescribing information as approved by the health authorities, such those issued by the FDA, or the EMA, which are incorporated here by their entirety.

Pharmaceutical Compositions

The SAE inhibitors and the anti-CD20 antibodies used in the methods and kits described herein can be formulated into pharmaceutical compositions suitable for administration. The pharmaceutical compositions may comprise pharmaceutically acceptable excipients. A pharmaceutically acceptable excipient, as used herein, includes, but are not limited to, any and all solvents, dispersion media, or other liquid vehicles, dispersion or suspension aids, diluents, granulating and/or dispersing agents, surface active agents, isotonic agents, thickening or emulsifying agents, preservatives, binders, lubricants or oil, coloring, sweetening or flavoring agents, stabilizers, antioxidants, antimicrobial or antifungal agents, osmolality adjusting agents, pH adjusting agents, buffers, chelants, cyoprotectants, and/or bulking agents, as suited to the particular dosage form desired. Various excipients for formulating pharmaceutical compositions and techniques for preparing the composition are known in the art (see Remington: The Science and Practice of Pharmacy, 21St Ed., A. R. Gennaro (Lippincott, Williams & Wilkins, Baltimore, MD), 2006; incorporated by reference in its entirety)

Any of the therapeutic agents described herein may be in the form of a pharmaceutically acceptable salt. In some embodiments, such salts are derived from inorganic or organic acids or bases. For reviews of suitable salts, see, e.g., Berge et al., J. Pharm. Sci., 1977, 66, 1-19 and Remington: The Science and Practice of Pharmacy, 20th Ed., A. Gennaro (ed.), Lippincott Williams & Wilkins (2000).

Examples of suitable acid addition salts include acetate, adipate, alginate, aspartate, benzoate, benzene sulfonate, bisulfate, butyrate, citrate, camphorate, camphor sulfonate, cyclopentanepropionate, digluconate, dodecylsulfate, ethanesulfonate, fumarate, lucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenyl-propionate, picrate, pivalate, propionate, succinate, tartrate, thiocyanate, tosylate and undecanoate.

Examples of suitable base addition salts include ammonium salts; alkali metal salts, such as sodium and potassium salts; alkaline earth metal salts, such as calcium and magnesium salts; salts with organic bases, such as dicyclohexylamine salts, N-methyl-D-glucamine; and salts with amino acids such as arginine, lysine, and the like.

For example, Berge lists the following FDA-approved commercially marketed salts: anions acetate, besylate (benzenesulfonate), benzoate, bicarbonate, bitartrate, bromide, calcium edetate (ethylenediaminetetraacetate), camsylate (camphorsulfonate), carbonate, chloride, citrate, dihydrochloride, edetate (ethylenediaminetetraacetate), edisylate (1,2-ethanedisulfonate), estolate (lauryl sulfate), esylate (ethanesulfonate), fumarate, gluceptate (glucoheptonate), gluconate, glutamate, glycollylarsanilate (glycollamidophenylarsonate), hexylresorcinate, hydrabamine (N,N'-di(dehydroabietyl)-ethylenediamine), hydrobromide, hydrochloride, hydroxynaphthoate, iodide, isethionate (2-hydroxyethanesulfonate), lactate, lactobionate, malate, maleate, mandelate, mesylate (methanesulfonate), methylbromide, methylnitrate, methylsulfate, mucate, napsylate (2-naphthalenesulfonate), nitrate, pamoate (embonate), pantothenate, phosphate/diphosphate, polygalacturonate, salicylate, stearate, subacetate, succinate, sulfate, tannate, tartrate, teoclate (8-chlorotheophyllinate) and triethiodide; organic cations benzathine (N,N'-dibenzylethylenediamine), chloroprocaine, choline, diethanolamine, ethylenediamine, meglumine (N-methylglucamine) and procaine; and metallic cations aluminum, calcium, lithium, magnesium, potassium, sodium and zinc.

Berge additionally lists the following non-FDA-approved commercially marketed (outside the United States) salts: anions adipate, alginate, aminosalicylate, anhydromethylenecitrate, arecoline, aspartate, bisulfate, butylbromide, camphorate, digluconate, dihydrobromide, disuccinate, glycerophosphate, hemisulfate, hydrofluoride, hydroiodide, methylenebis(salicylate), napadisylate (1,5-naphthalenedisulfonate), oxalate, pectinate, persulfate, phenylethylbarbiturate, picrate, propionate, thiocyanate, tosylate and undecanoate; organic cations benethamine (N-benzylphenethylamine), clemizole (1-p-chlorobenzyl-2-pyrrolildine-1'-ylmethylbenzimidazole), diethylamine, piperazine and tromethamine (tris(hydroxymethyl)aminomethane); and metallic cations barium and bismuth.

The pharmaceutical compositions may comprise pharmaceutically acceptable carriers. As used herein, "pharmaceutically acceptable carrier" refers to a material that is compatible with a recipient subject (a human) and is suitable for delivering an active agent to the target site without terminating the activity of the agent. The toxicity or adverse effects, if any, associated with the carrier preferably are commensurate with a reasonable risk/benefit ratio for the intended use of the active agent.

Pharmaceutically acceptable carriers that may be used in these compositions include ion exchangers, alumina, aluminum stearate, lecithin, serum proteins, such as human serum albumin, buffer substances such as phosphates or carbonates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The pharmaceutical compositions for use in the methods of the present disclosure may be manufactured by methods well known in the art such as conventional granulating, mixing, dissolving, encapsulating, lyophilizing, or emulsifying processes, among others. Compositions may be produced in various forms, including granules, precipitates, or particulates, powders, including freeze dried, rotary dried or spray dried powders, amorphous powders, tablets, capsules, syrup, suppositories, injections, emulsions, elixirs, suspensions or solutions. Formulations may contain stabilizers, pH modifiers, surfactants, solubilizing agents, bioavailability modifiers and combinations of these. These pharmaceutical compositions are formulated for pharmaceutical administration to a human being. Such compositions may be administered orally, parenterally, by inhalation spray, topically, rectally, nasally, buccally, vaginally or via an implanted reservoir. The term "parenteral" as used herein includes subcutaneous, intravenous, intraperitoneal, intramuscular, intra-articular, intra-synovial, intrasternal, intrathecal, intrahepatic, intralesional and intracranial injection or infusion techniques. In some embodiments, the compositions are administered orally, intravenously or subcutaneously. In some embodiments, the compositions are administered orally. In some embodiments, the compositions are administered intravenously. In some embodiments, the intravenous administration can be intravenous infusion or intravenous injection. In some embodiments, the compositions are administered by an intravenous infusion. In some embodiments, the compositions are administered by an intravenous injection. In some embodiments, the compositions are administered by subcutaneous injection. In some embodiments, the compositions are administered by intravenous infusion and then subsequently administered by subcutaneous injection. In another embodiment, the anti-CD20 antibody is coadministered with human hyaluronidase subcutaneously. These formulations may be designed to be short-acting, fast-releasing, or long-acting. Furthermore, the compositions may be administered in a local rather than systemic means, such as administration (e.g., by injection) at a tumor site.

Pharmaceutical formulations may be prepared as liquid suspensions or solutions using a liquid, such as an oil, water, an alcohol, and combinations of these. Solubilizing agents such as cyclodextrins may be included. Pharmaceutically suitable surfactants, suspending agents, or emulsifying agents, may be added for oral or parenteral administration. Suspensions may include oils, such as peanut oil, sesame oil, cottonseed oil, corn oil and olive oil. Suspension preparations may also contain esters of fatty acids such as ethyl oleate, isopropyl myristate, fatty acid glycerides and acetylated fatty acid glycerides. Suspension formulations may include alcohols, such as ethanol, isopropyl alcohol, hexadecyl alcohol, glycerol and propylene glycol; ethers, such as poly(ethyleneglycol); petroleum hydrocarbons such as mineral oil and petrolatum; and water.

Sterile injectable forms of these pharmaceutical compositions may be aqueous or oleaginous suspensions. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as sorbitan alkyl esters, such as Tweens or Spans, and other emulsifying agents or bioavailability enhancers which are commonly used in the manufacture of pharmaceutically acceptable solid, liquid, or other dosage forms may also be used for the purposes of formulation. Compounds may be formulated for parenteral administration by injection such as by bolus injection or continuous infusion. A unit dosage form for injection may be in ampoules or in multi-dose containers.

These pharmaceutical compositions may be orally administered in any orally acceptable dosage form including capsules, tablets, aqueous suspensions or solutions. When aqueous suspensions are required for oral use, the active ingredient is combined with emulsifying and suspending agents. If desired, certain sweetening, flavoring or coloring agents may also be added. For oral administration in a capsule form, useful diluents include lactose and dried cornstarch. In the case of tablets for oral use, carriers that are commonly used include lactose and corn starch. Lubricating agents, such as magnesium stearate, are also typically added. Coatings may be used for a variety of purposes, e.g., to mask taste, to affect the site of dissolution or absorption, or to prolong drug action. Coatings may be applied to a tablet or to granulated particles for use in a capsule.

Alternatively, these pharmaceutical compositions may be administered in the form of suppositories for rectal administration. These may be prepared by mixing the agent with a suitable non-irritating excipient which is solid at room temperature but liquid at rectal temperature and therefore will melt in the rectum to release the drug. Such materials include cocoa butter, beeswax and polyethylene glycols.

These pharmaceutical compositions may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract may be affected in a rectal suppository formulation (see above) or in a suitable enema formulation. Topically-transdermal patches may also be used. For topical applications, the pharmaceutical compositions may be formulated in a suitable ointment containing the active component suspended or dissolved in one or more carriers. Carriers for topical administration of the compounds of the present disclosure include mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active component(s) suspended or dissolved in one or more pharmaceutically acceptable carriers. Suitable carriers include mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions may also be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In one embodiment, a compound of formula I-263a is formulated as a solution for intravenous infusion. In some embodiments, a compound of formula I-263a is formulated in a solution with a buffering agent or a PH modifying agent, and a cyclodextrin, such as a beta-cyclodextrin. In one embodiment, the solution includes phosphoric acid and Captisol (betadex sulfobutyl ether sodium) in water.

In some embodiments, a compound of formula I-263a is formulated as a drug product, wherein the drug product contains compound I-263a in a solution of phosphoric acid and Captisol (betadex sulfobutyl ether sodium) in water. In some embodiments, the drug product is packaged with a volume of 10 mL of compound I-263a sterile solution.

Kits

In some embodiments, the SAE inhibitor or the anti-CD20 antibody described herein may be manufactured for inclusion in a kit. A "kit" is any article of manufacture (e.g., a package or container) comprising at least one reagent or chemotherapeutic agent. A kit for use in the methods herein may comprise an SAE inhibitor, such as a compound of formula I-263a or a pharmaceutically acceptable salt thereof. In some embodiments, the kit may further include an anti-CD20 antibody, and optionally one or more additional therapeutic agents. In some embodiments, the kit may include a compound of formula I-263a or a pharmaceutically acceptable salt thereof, an anti-CD20 antibody, and optionally one or more additional therapeutic agents. In some embodiments, the kit may include one or more SAE inhibitors or pharmaceutically acceptable salts thereof. In some embodiments, the kit may include one or more anti-CD20 antibodies.

In some embodiments, the present disclosure relates to a kit comprising a medicament for use in treating cancer or autoimmune disease in a patient in need of such treatment. The kit comprises a medicament comprising an SAE inhibitor, and instructions for administering the SAE inhibitor and an anti-CD20 antibody; or the kit comprises a medicament comprising an anti-CD20 antibody, and instructions for administering the anti-CD20 antibody and an SAE inhibitor. The kit may contain a medicament comprising an SAE inhibitor and an anti-CD20 antibody, and instructions for administering the SAE inhibitor and the anti-CD20 antibody, wherein the medicament is in single dosage form or in separate dosage forms. In some embodiments, the kit optionally comprises one or more additional therapeutic agents.

In some embodiments, a kit comprising an SAE inhibitor and an anti-CD20 antibody may further include another component or reagent. In some embodiments, a reagent in the kit may be a diluent for preparing the SAE inhibitor for administration. In some embodiments, a reagent in the kit may be a diluent for preparing the anti-CD20 antibody for administration. In some embodiments, a component in the kit may be a vessel for mixing the combination of the SAE inhibitor and the anti-CD20 antibody.

In another aspect, the present disclosure relates to a kit for treating cancer or autoimmune disease comprising at least one medicament comprising at least one dose of Compound I-263a or a pharmaceutically acceptable salt thereof, and at least one medicament comprising at least one dose of an anti-CD20 antibody, said kit for treating cancer further comprising dosing instructions for administering the medicaments for treatment of the patient in recognized need thereof.

In order that this present disclosure be more fully understood, the following examples are set forth. These examples are illustrative only and are not intended to limit the scope of the present disclosure in any way.

Examples

Abbreviations
H hour
Min minutes
HPLC High-pressure liquid chromatography
UPLC Ultra-pressure liquid chromatography
NMR Nuclear Magnetic Resonance
THF tetrahydrofuran
WFI Water for Injection
TGI tumor growth inhibition
Mg milligram
$mm^3$ cubic millimeter
HPbCD 2-hydroxypropyl-ß-cyclodextrin
CMC carboxymethylcellulose PO oral
SC subcutaneously
SD starting day
CD20+ CD20-positive
NHL non-Hodgkin lymphoma
aNHL aggressive non-Hodgkin lymphoma
iNHL indolent non-Hodgkin lymphoma
r/r relapsed or refractory
BLRM Bayesian Logistic Regression Modeling
MTD maximum tolerated dose
PAD pharmacologically active dose
IV intravenous
AE adverse events
DLT Dose limiting toxicity
PK Pharmacokinetic
CST clinical study team
TEAEs Treatment-emergent adverse events
DL Dose level
C1D1 Cycle one, day one
IRR infusion-related reaction
CRS cytokine release syndrome
ORR overall response rate Example 1: In Vivo Tumor Efficacy General Analytical Methods Unless otherwise stated H NMR spectra were obtained using a Varian 300 MHz. Unless otherwise stated HPLC were obtained on Agilent 1100 Series and UPLC were obtained by Water Acuity Systems.

Compound I-263a, as used in the Examples below, can be synthesized according to the procedures recited in Example 201 in PCT publication number WO 2016/004136.

General Experimental Conditions for in vivo Tumor Efficacy Models

Xenograft Models

The following Xenograft models were utilized in each of Studies 1-6, as specified below.

OCI-Ly 10 Study 1: OCI-Ly 10 is a human diffuse large B-cell lymphoma cell-line derived xenograft. 6 week old female SCID mice (Beijing HFK Bioscience Co., Ltd.) were inoculated subcutaneously in the right flank (cell suspension) with $4\times10^6$ OCI-Ly10 cells. When the mean tumor volume reached approximately 200 mm$^3$, the animals were randomized into treatment and control groups (n=7/group). Tumor growth inhibition and body weight change were calculated on Day 21 of treatment. Tumor volumes below the humane end-point for size were continually monitored following the end of treatment (post-treatment period) to a maximum of 120 days post treatment initiation. The number of days from the initiation of treatment for the average tumor volume to reach 1000 mm$^3$ was noted for each group.

OCI-Ly10 Study 2: OCI-Ly 10 is a human diffuse large B-cell lymphoma cell-line derived xenograft. 8 week old female SCID mice (Beijing HFK Bioscience Co., Ltd.) were inoculated subcutaneously in the right flank (cell suspension) with $4\times10^6$ OCI-Ly 10 cells. When the mean tumor volume reached approximately 200 mm$^3$, the animals were randomized into treatment and control groups (n=8/group). Tumor growth inhibition and body weight change were calculated on Day 21 of treatment. Tumor volumes below the humane end-point for size were continually monitored following the end of treatment (post-treatment period) to a maximum of 120 days post treatment initiation. The number of days from the initiation of treatment for the average tumor volume to reach 1000 mm$^3$ was noted for each group.

WSU-DLCL2 Study 3: WSU-DLCL2 is a human diffuse large B-cell lymphoma cell-line derived xenograft. 7 week old female SCID mice (Charles River Laboratories) were inoculated subcutaneously in the right flank (cell suspension with $4.0\times10^6$ cells). When the mean tumor volume reached approximately 200 mm$^3$, the animals were randomized into treatment groups and control groups (n=8/group). Tumor growth inhibition and body weight change were calculated on Day 21 of treatment. Tumor volumes below the humane end-point for size were continually monitored following the end of treatment (post-treatment period) for an additional week. The number of days from the initiation of treatment for the average tumor volume to reach 1000 mm$^3$ was noted for each group.

TMD8 Study 4: TMD8 is a human diffuse large B-cell lymphoma cell-line derived xenograft. 8 week old female SCID mice (Beijing HFK Bioscience Co., Ltd) were inoculated subcutaneously in the right flank (cell suspension with $4\times10^6$ cells). When the mean tumor volume reached approximately 190 mm$^3$, the animals were randomized into treatment groups and control groups (n=8/group). Tumor growth inhibition and body weight change were calculated on Day 18 of treatment. Tumor volumes below the humane end-point for size were continually monitored following the end of treatment (post-treatment period) for an additional week. The number of days from the initiation of treatment for the average tumor volume to reach 1000 mm$^3$ was noted for each group.

PHTX-166L Study 5: PHTX-166L is a human patient-derived B-cell lymphoma primary xenograft. Small tumor pieces measuring approximately 2 mm×2 mm were implanted subcutaneousy on the right flank via trocar injection. When the mean tumor volume reached approximately 160 mm$^3$, the animals were randomized into treatment groups and control groups (n=7/group). Tumor growth inhibition and body weight change were calculated on Day 11 of treatment. Tumor volumes below the humane end-point for size were continually monitored following the end of treatment (post-treatment period) until Day 146 post treatment initiation. The number of days from the initiation of treatment for the average tumor volume to reach 1000 mm$^3$ was noted for each group.

PHTX-166L Study 6: PHTX-166L is a human patient-derived primary B-cell lymphoma xenograft. Small tumor pieces measuring approximately 2 mm×2 mm were implanted subcutaneousy on the right flank via trocar injection. When the mean tumor volume reached approximately 160 mm$^3$, the animals were randomized into treatment groups and control groups (n=6/group). Tumor growth inhibition and body weight change were calculated on Day 9 of treatment. Tumor volumes below the humane end-point for size were continually monitored following the end of treatment (post-treatment period) until Day 35 post treatment initiation. The number of days from the initiation of treatment for the average tumor volume to reach 1000 mm$^3$ was noted for each group.

Test Agents

The following test agents were utilized in each of Studies 1-6, as specified below.

Study 1: A 2.5 mg/mL or 1.5 mg/mL stock solution of compound I-263a was formulated weekly in 20% HPBCD and administered intravenously based on exact animal body weight on each day of treatment, using a dosing volume of 10 mL/kg body weight. Final doses received were 25 mg/kg or 15 mg/kg, respectively. Dosing volume for Compound I-263a was 0.2 mL. Rituximab (available from multiple vendors, including Roche Diagnostics GmbH and Myoderm, Norriston, PA) was formulated prior to each injection at 1.0 mg/mL in 0.9% saline and administered intravenously based on exact body weight on each day of treatment, using a dosing volume of 10 mL/kg resulting in a 10 mg/kg dose. Dosing volume for rituximab was 0.2 mL. Compound I-263a and rituximab were administered IV on a QW schedule for 3 weeks (Day 1, 8, and 15).

Study 2: A 1.0 mg/mL or 0.5 mg/mL stock solution of compound I-263a was formulated weekly in 20% HPβCD and administered intravenously based on exact animal body weight on each day of treatment, using a dosing volume of 10 mL/kg body weight. Final doses received were 10 mg/kg or 5 mg/kg, respectively. Dosing volume for Compound I-263a was 0.2 mL. Rituximab (available from multiple vendors, including Roche Diagnostics GmbH and Myoderm, Norriston, PA) was formulated prior to each injection at 0.5 mg/mL in 0.9% saline and administered intravenously based on exact body weight on each day of treatment, using a dosing volume of 10 mL/kg resulting in a 5 mg/kg dose. Dosing volume for Rituximab was 0.2 mL. Compound I-263a and rituximab were administered IV on a QW schedule for 3 weeks (Day 1, 8, and 15).

Study 3: A 0.48 mg/mL stock solution of Compound I-263a was formulated weekly in 20% HPβCD and administered intravenously based on average body weight resulting in a 5 mg/kg dose. Dosing volume for Compound I-263a was 0.2 mL. Rituximab (available from multiple vendors, including Roche Diagnostics GmbH and Myoderm, Norriston, PA) was formulated prior to each injection at 0.48 mg/mL in 0.9% saline and administered intravenously based on average body weight resulting in a 5 mg/kg dose. Dosing volume for Rituximab was 0.2 mL. Compound I-263a and rituximab were administered IV on a QW schedule for 3 weeks (Days 1, 8, and 15).

Study 4: A 2.5 mg/mL or 1.5 mg/mL stock solution of compound I-263a was formulated weekly in 20% HPβCD and administered intravenously based on exact animal body weight on each day of treatment, using a dosing volume of 10 mL/kg body weight. Final doses received were 25 mg/kg or 15 mg/kg, respectively. Dosing volume for Compound I-263a was 0.2 mL. Rituximab (available from multiple vendors, including Roche Diagnostics GmbH and Myoderm, Norriston, PA) was formulated prior to each injection at 1.0 mg/mL in 0.9% saline and administered intravenously based on exact body weight on each day of treatment, using a dosing volume of 10 mL/kg resulting in a 10 mg/kg dose. Dosing volume for Rituximab was 0.2 mL. Compound I-263a and rituximab were administered IV on a QW schedule for 3 weeks (Day 1, 8, and 15).

Study 5: A 5.75 mg/mL and 2.88 mg/mL stock solution of Compound I-263a was formulated weekly in 20% HPβCD and administered intravenously based on average body weight resulting in a 25 mg/kg and 12.5 mg/kg dose, respectively. Dosing volume for Compound I-263a was 0.1 mL. Rituximab (available from multiple vendors, including Roche Diagnostics GmbH and Myoderm, Norriston, PA) was formulated prior to each injection at 2.1 mg/mL in 0.9% saline and administered intravenously based on average body weight resulting in a 10 mg/kg dose. Dosing volume for Rituximab was 0.1 mL. Compound I-263a and rituximab were administered IV on a QW schedule for 1 week (Days 1 and 8).

Study 6: A 0.5 mg/mL stock solution of Compound I-263a was formulated weekly in 20% HPβCD and administered intravenously based on average body weight resulting in a 5.0 mg/kg dose. Dosing volume for Compound I-263a was 0.2 mL. Rituximab (available from multiple vendors, including Roche Diagnostics GmbH and Myoderm, Norriston, PA) was formulated prior to each injection at 0.5 mg/mL in 0.9% saline and administered intravenously based on average body weight resulting in a 5.0 mg/kg dose. Dosing volume for Rituximab was 0.2 mL. Compound I-263a and rituximab were administered IV on a QW schedule for 1 week (Days 1 and 8).

Tumor Measurements:

Tumors were measured twice weekly using vernier calipers. Tumor volumes were calculated using standard procedures $V=W^2 \times L/2$, where V=volume, W=width, and L=length for the tumor xenograft. When mean tumor volumes reached approximately 200 mm$^3$ for studies 1, 2 and 3, 190 mm$^3$ for study 4, 160 mm$^3$ for study 5, or 145 mm$^3$ for study 6, mice were randomized into groups of n=4 or 6/arm as described in Table 1a, 2a, 3a, 4a, 5a, or 6a, and dosed with vehicle (20% HPβCD), Compound I-263a, rituximab, or the combination of I-263a plus rituximab at various doses and schedules as described below in Table 1a, 2a, 3a, 4a, 5a, or 6a. Tumor size and body weight were measured twice a week for the duration of the study. Mice were euthanized when the average tumor volume of a treatment or control group reached approximately 1000 mm$^3$ or when an individual tumor exceeded the humane end-point for size. The antitumor activity was determined by calculating the percent tumor growth inhibition (TGI) on Day 21 for studies 1, 2, and 3, Day 18 for study 4, Day 11 for study 5, or Day 9 for study 6, using the mean tumor volumes (MTV) in the following equation:

Percent TGI=(MTV Vehicle group−MTV Treatment group)÷MTV Vehicle group×100

MTV and TGI values are shown in Table 1a, 2a, 3a, 4a, 5a, and 6a. Mean tumor volume for the complete duration of the study is reported as a function of time in FIGS. 1a and 1b, 2b, 3b, 4b, 5b, and 6b.

Statistical Analysis of Treatment and Combination Effect for Tumor Growth in Subcutaneous Xenograft Models The following statistical analysis methods were utilized in each of Studies 1-6.

All tumor volumes had a value of 1 added to them before $\log_{10}$ transformation. These values were compared across treatment groups to assess whether the differences in the trends over time were statistically significant. To compare pairs of treatment groups, the following mixed-effects linear regression model was fit to the data using the maximum likelihood method:

$$Y_{ijk} - Y_{i0k} = Y_{i0k} + \text{treat}_i + \text{day}_j + \text{day}_j^2 + (\text{treat}^*\text{day})_{ij} + (\text{treat}^*\text{day}^2)_{ij} + e_{ijk} \qquad (1)$$

where $Y_{ijk}$ is the $\log_{10}$ tumor value at the $j^{th}$ time point of the $k^{th}$ animal in the $i^{th}$ treatment, $Y_{i0k}$ is the day 0 (baseline) $\log_{10}$ tumor value in the $k^{th}$ animal in the $i^{th}$ treatment, day$_j$ was the median-centered time point and (along with day$_j^2$) was treated as a continuous variable, and $e_{ijk}$ is the residual error. A spatial power law covariance matrix was used to account for the repeated measurements on the same animal over time. Interaction terms as well as day$_j^2$ terms were removed if they were not statistically significant.

A likelihood ratio test was used to assess whether a given pair of treatment groups exhibited differences which were statistically significant. The −2 log likelihood of the full model was compared to one without any treatment terms (reduced model) and the difference in the values was tested using a Chi-squared test. The degrees of freedom of the test were calculated as the difference between the degrees of freedom of the full model and that of the reduced model.

The predicted differences in the log tumor values ($Y_{ijk}-Y_{i0k}$, which can be interpreted as $\log_{10}$ (fold change from day 0)) were taken from the above models to calculate mean AUC values for each treatment group. A dAUC value was then calculated as:

$$dAUC = \frac{\text{mean}(AUC_{ctl}) - \text{mean}(AUC_{trt})}{\text{mean}(AUC_{ctl})} * 100 \quad (2)$$

This assumed $AUC_{ctl}$ was positive. In instances where $AUC_{ctl}$ was negative, the above formula was multiplied by $-1$. P values <0.05 were considered significant.

For synergy analyses, the observed differences in the log tumor values were used to calculate AUC values for each animal. In instances when an animal in a treatment group was removed from the study, the last observed tumor value was carried forward through all subsequent time points. The AUC for the control, or vehicle, group was calculated using the predicted values from the pairwise models described above. We defined a measure of synergy as follows:

$$Frac_{A_k} = \frac{AUC_{ctl} - AUC_{A_k}}{AUC_{ctl}} \quad (3)$$

$$Frac_{B_k} = \frac{AUC_{ctl} - AUC_{B_k}}{AUC_{ctl}} \quad (4)$$

$$Frac_{AB_k} = \frac{AUC_{ctl} - AUC_{AB_k}}{AUC_{ctl}} \quad (4)$$

synergy score = $(\text{mean}(Frac_A) + (\text{mean}(Frac_B) - \text{mean}(Frac_{AB})) * 100$ (6)

where $A_k$ and $B_k$ are the $k^{th}$ animal in the individual treatment groups and $AB_k$ is the $k^{th}$ animal in combination treatment group. $AUC_{ctl}$ is the model-predicted AUC for the control group and was treated as a constant with no variability. The standard error of the synergy score was calculated as the square root of the sum of squared standard errors across groups A, B, and AB. The degrees of freedom were estimated using the Welch-Satterthwaite equation. A hypothesis test was performed to determine if the synergy score differed from 0. P values were calculated by dividing the synergy score by its standard error and tested against a t-distribution (two-tailed) with the above-calculated degrees of freedom. P values <0.05 were considered significant.

The effect was classified into four different categories. It was considered synergistic if the synergy score was less than 0 and additive if the synergy score wasn't statistically different from 0. If the synergy score was greater than zero, but the mean AUC for the combination was lower than the lowest mean AUC among the two single agent treatments, then the combination was sub-additive. If the synergy score was greater than zero, and the mean AUC for the combination was greater than the mean AUC for at least one of the single agent treatments, then the combination was antagonistic.

Results

Mouse xenograft models, performed as described in the general methods above, were used to assess the combination effect in vivo of Compound I-263a and rituximab. The details for each study are as shown below in Tables 1a, 2a, 3a, 4a, 5a, and 6a. The results were analyzed using the statistical analysis described above and the classification of the combination for the treatment period is shown below in Tables 1b, 2b, 3b, 4b, 5b, and 6b.

Tumor growth curves are shown during the treatment period in FIG. 1a, 2a, 3, 4a, 5a, and 6a. Tumor growth curves for treatment and post-treatment periods are shown in FIGS. 1b, 2b, 4b, 5b, and 6b. In addition to the combination classification shown in Tables 1b, 2b, 3b, 4b, 5b, and 6b, the tumor growth curves for the post-treatment periods are also indicative of the combination effect, capturing a broader temporal spectrum of tumor response to drug treatment.

Study 1: OCI-Ly10 Xenograft Model

In the OCI-Ly 10 diffuse large B-cell lymphoma xenograft model, mice were inoculated, randomized on Day 0 (14 days post inoculation), and treatments began on Day 1 for all groups. Compound I-263a was tested at 25 mg/kg and 15 mg/kg administered IV on a QW (once per week) schedule. Rituximab was tested at 10 mg/kg administered IV on a QW schedule. In the combination treatment group, Compound I-263a was administered first, followed immediately by the administration of rituximab. One group served as the vehicle-treated group (Group 1) receiving IV treatment with the vehicle for I-263a (20% HPβCD) on a QW schedule.

The combination arms of Compound I-263a with rituximab yielded additive effects during the 21-day treatment phase of the study. Post-treatment measurements were taken through Day 120. In both combination arms, all mice achieved complete regressions of their tumors which were maintained to Day 120. All single-agent I-263a treated mice were euthanized by Day 120 once the group sized reached 1000 mm³ or an individual tumor volume exceeded the humane end-point for size.

Figure 1B:
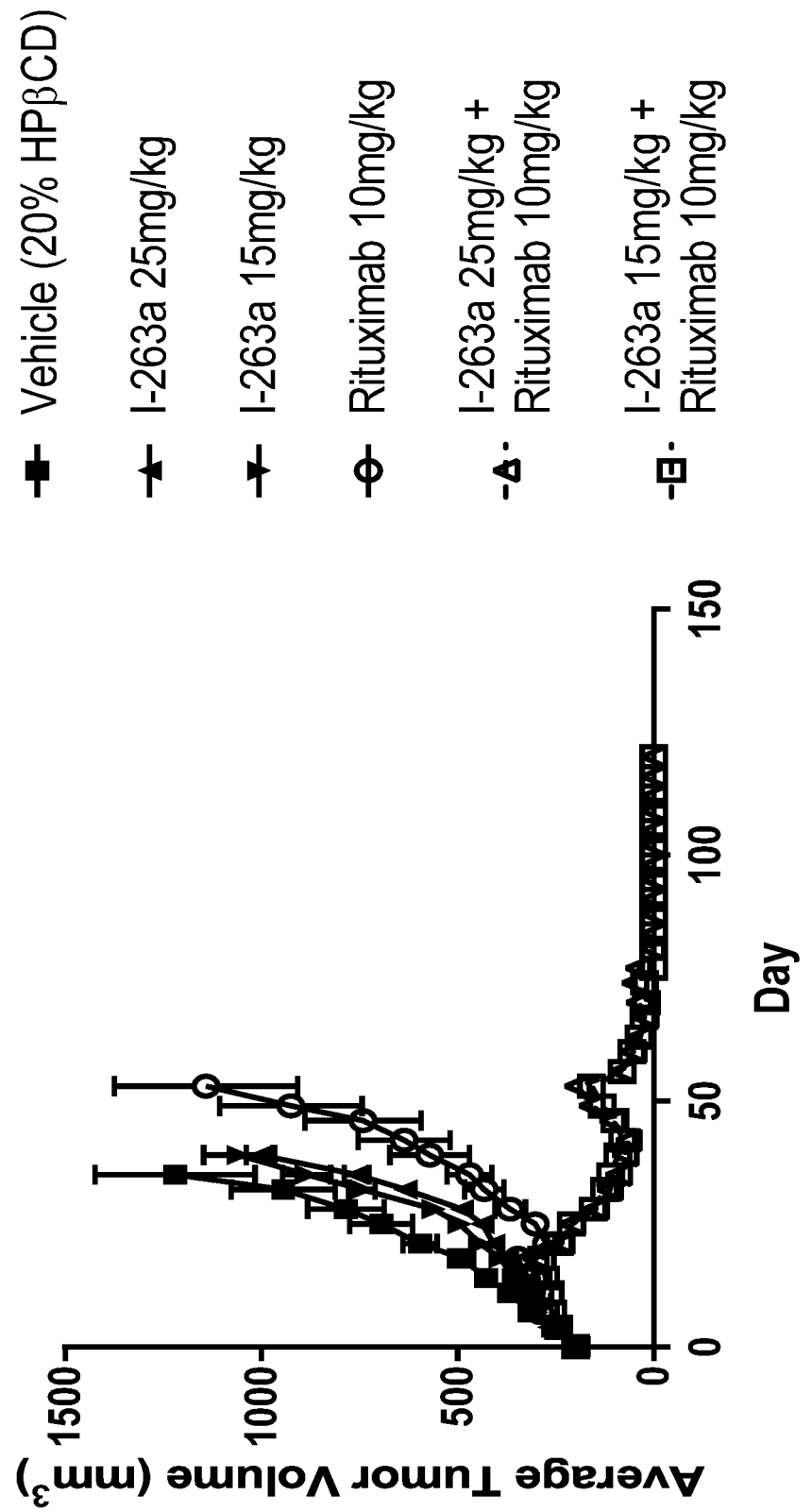
FIG. 1b shows a plot of tumor volume as a function of time during treatment and post-treatment periods in a OCI-Ly 10 xenograft model following administration of Compound I-263a and rituximab to mice.

The treatment groups from Study 1 are shown in Table 1a. The combination effect for the treatment period is shown in Table 1b. Tumor growth curves are shown during the treatment period in FIG. 1a. Tumor growth curves for treatment and post-treatment periods are shown in FIG. 1b.

TABLE 1a

Combination of Compound I-263a and rituximab in the OCI-Ly10 xenograft model

| Study Group | Treatment | Dosing Regimen | Route | Tumor volume on Day 21 (±SEM) | TGI % | dAUC | P-value | Days to 1000 mm³ MTV |
|---|---|---|---|---|---|---|---|---|
| A | 20% HPβCD | QW | IV | 596.7 ± 43.4 | NA | NA | NA | 32.6 |
| B | I-263a 25 mg/kg | QW | IV | 409.7 ± 19.2 | 31.3 | 23.6 | p < 0.001 | 39 |

TABLE 1a-continued

Combination of Compound I-263a and rituximab in the OCI-Ly10 xenograft model

| Study Group | Treatment | Dosing Regimen | Route | Tumor volume on Day 21 (±SEM) | TGI % | dAUC | P-value | Days to 1000 mm³ MTV |
|---|---|---|---|---|---|---|---|---|
| C | I-263a 15 mg/kg | QW | IV | 443.7 ± 12.3 | 25.6 | 21.4 | p < 0.05 | 37.6 |
| D | Rituximab 10 mg/kg | QW | IV | 274.4 ± 26.8 | 54 | 36.9 | p < 0.001 | 50.4 |
| E | I-263a 25 mg/kg, Rituximab 10 mg/kg | QW, QW | IV, IV | 236.4 ± 9.8 | 60.4 | 48.4 | p < 0.001 | >120 |
| F | I-263a 15 mg/kg, Rituximab 10 mg/kg | QW, QW | IV, IV | 242 ± 13.3 | 59.4 | 58.4 | p < 0.001 | >120 |

TABLE 1b

Classification for in vivo combination of Compound I-263a and rituximab in the OCI-Ly10 xenograft model

| Treatment | Synergy score | SEM | P-value | Classification |
|---|---|---|---|---|
| I-263a 25 mg/kg, Rituximab 10 mg/kg | 9.8 | 12.8 | 0.456 | Additive |
| I-263a 15 mg/kg, Rituximab 10 mg/kg | −1.8 | 13.3 | 0.896 | Additive |

Study 2: OCI-Ly10 Xenograft Model

In the OCI-Ly 10 diffuse large B-cell lymphoma xenograft model, mice were inoculated, randomized on Day 0 (30 days post inoculation), and treatments began on Day 1 for all groups. Compound I-263a was tested at 10 mg/kg and 5 mg/kg administered IV on a QW (once per week) schedule. Rituximab was tested at 5 mg/kg administered IV on a QW schedule. In the combination treatment group, Compound I-263a was administered first, followed immediately by the administration of rituximab. One group served as the vehicle-treated group (Group 1) receiving IV treatment with the vehicle for I-263a (20% HPβCD) on a QW schedule.

The combination arm of Compound I-263a at 10 mg/kg with rituximab at 5 mg/kg yielded synergistic effects during the 21-day treatment phase of the study. By Day 120, 7/8 mice achieved complete regressions of their tumors. The combination arms of Compound I-263a at 5 mg/kg with rituximab at 5 mg/kg yielded additive effects during the 21-day treatment phase of the study. By Day 120, 6/8 mice achieved complete regressions of their tumors. All single-agent I-263a treated mice were euthanized by Day 35 once the group sized reached 1000 mm³ or an individual tumor volume exceeded the humane end-point for size. All mice receiving single-agent rituximab treatment were euthanized on Day 77 (3/8 rituximab treated mice had complete regressions of their tumors on Day 77).

Figure 2A:
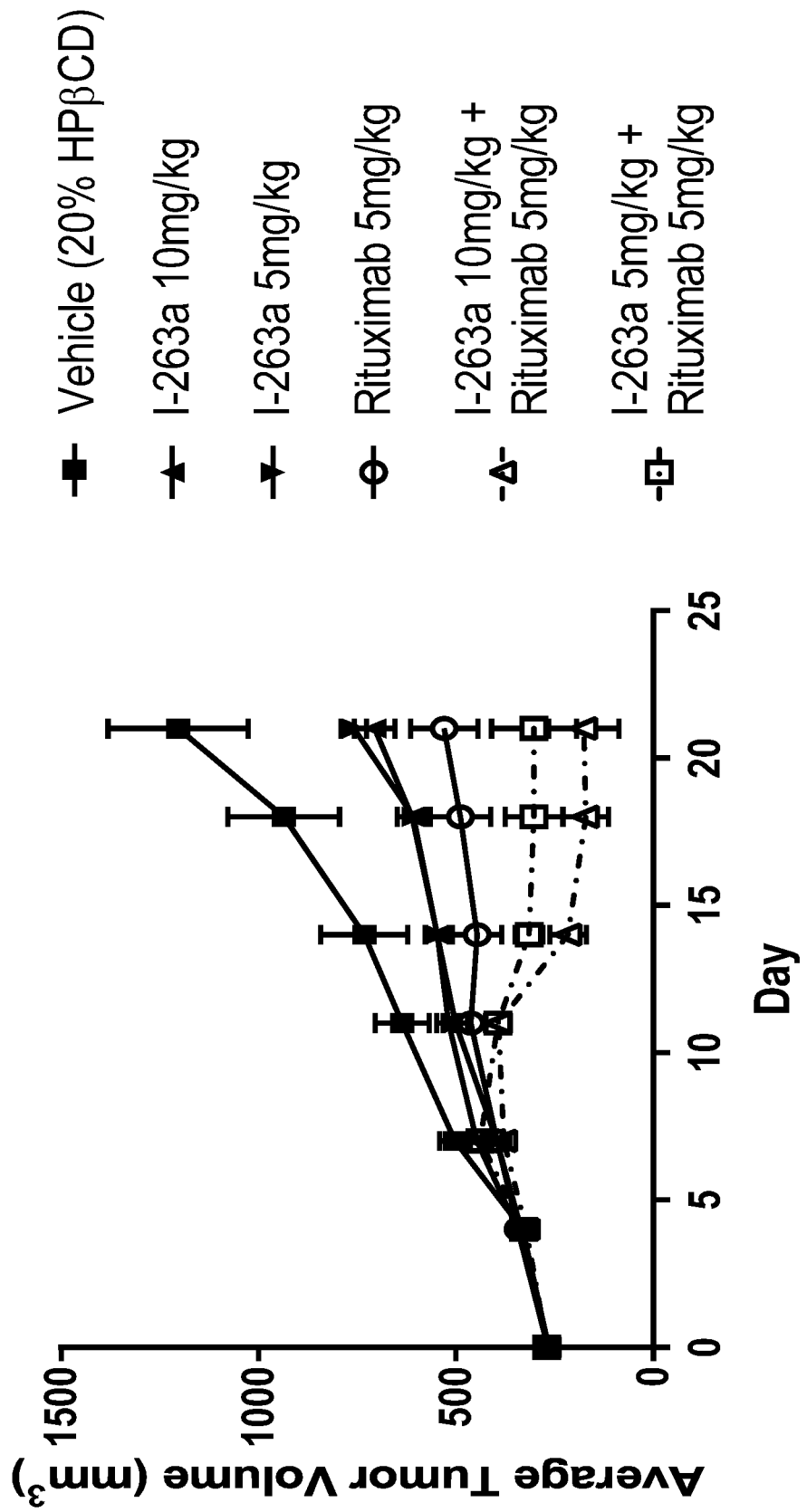
FIG. 2a shows a plot of tumor volume as a function of time during treatment period in a OCI-Ly 10 xenograft model following administration of Compound I-263a and rituximab to mice.
Figure 2B:
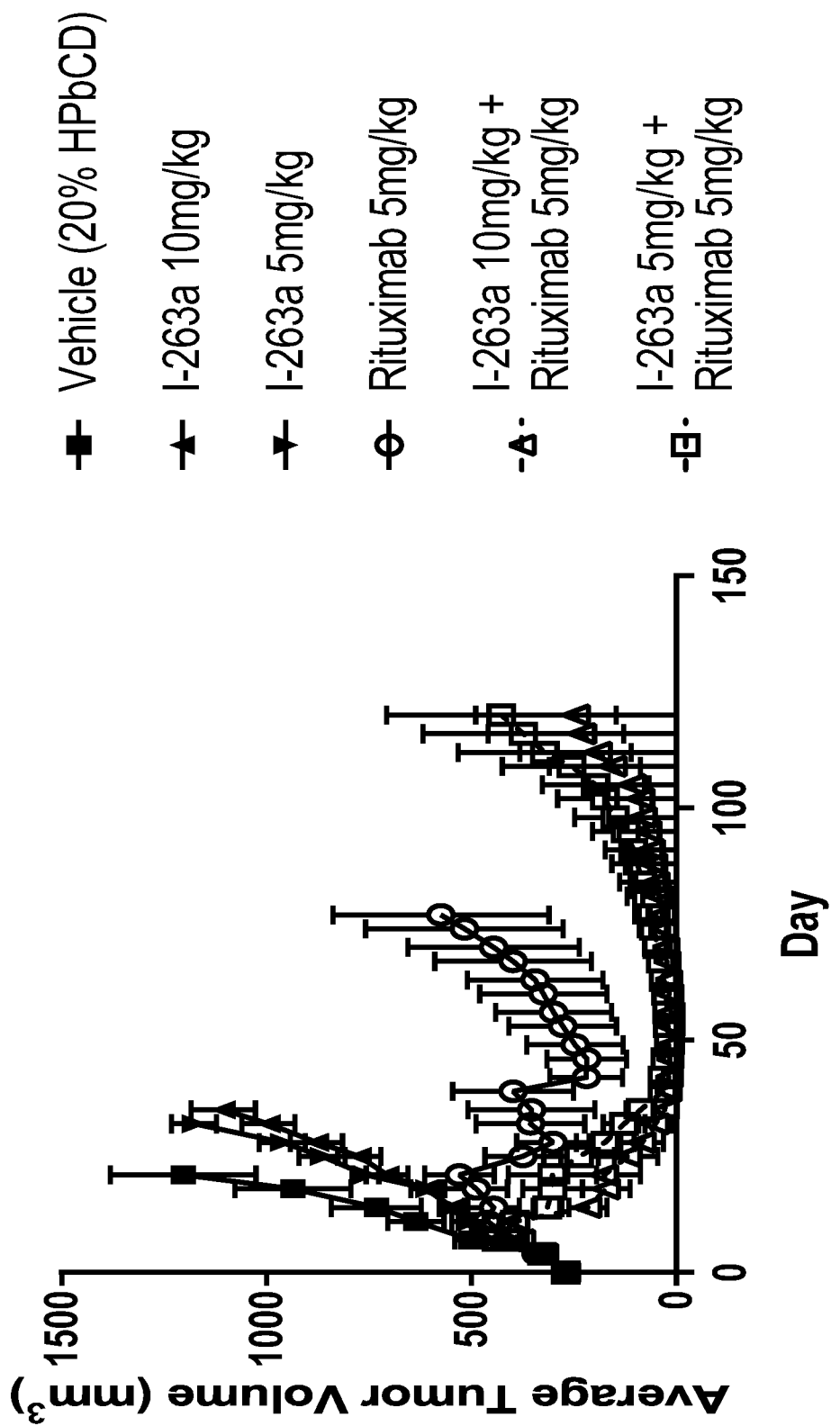
FIG. 2b shows a plot of tumor volume as a function of time during treatment and post-treatment periods in a OCI-Ly 10 xenograft model following administration of Compound I-263a and rituximab to mice.
Figure 3:
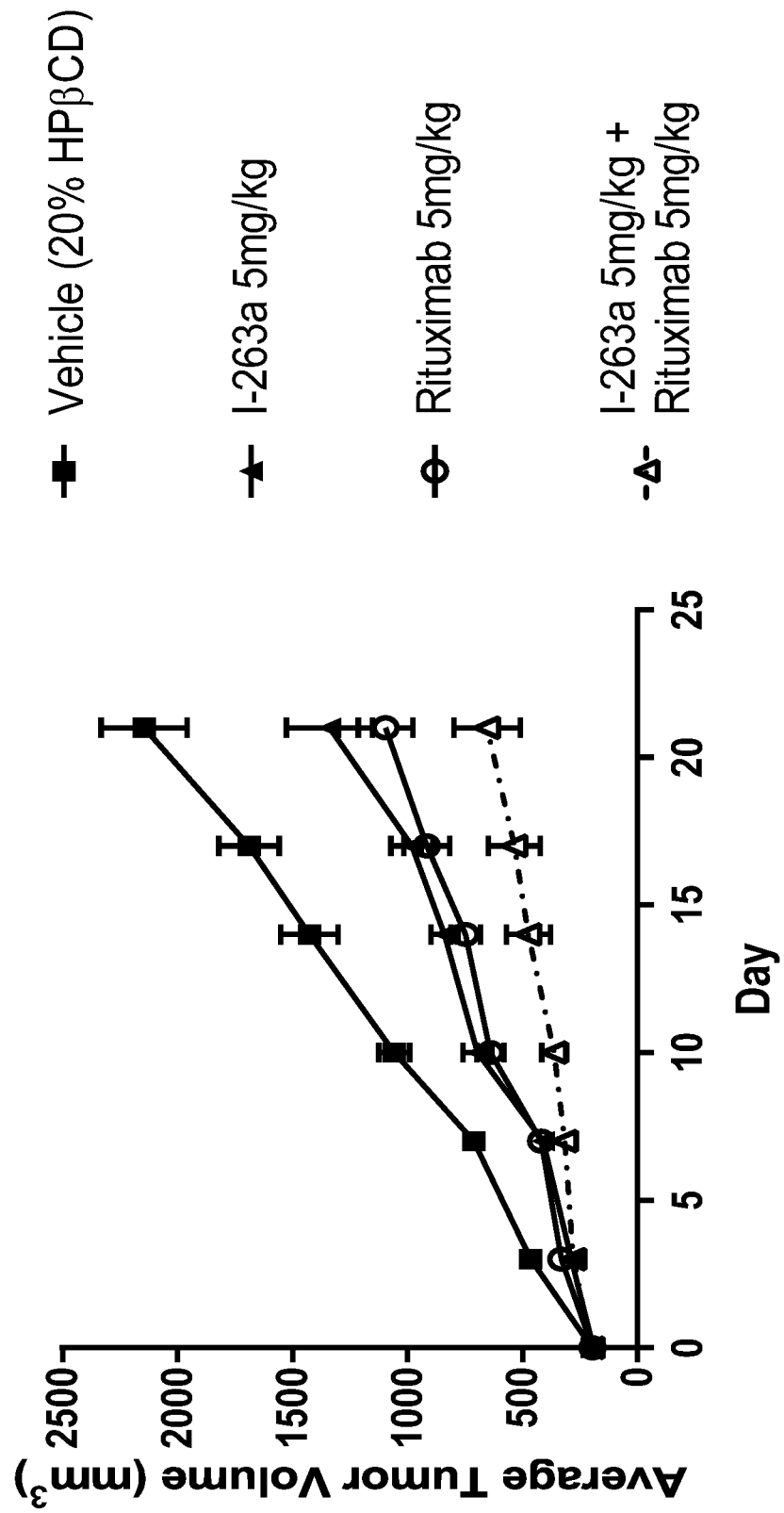
FIG. 3 shows a plot of tumor volume as a function of time during treatment period in a WSU-DLCLS xenograft model following administration of Compound I-263a and rituximab to mice.

The treatment groups from Study 2 are shown in Table 2a. The combination effect for the treatment period is shown in Table 2b. Tumor growth curves are shown during the treatment period in FIG. 2a. Tumor growth curves for treatment and post-treatment periods are shown in FIG. 2b.

TABLE 2a

Combination of Compound I-263a and rituximab in the OCI-Ly10 xenograft model

| Study Group | Treatment | Dosing Regimen | Route | Tumor volume on Day 21 (±SEM) | TGI % | dAUC | P-value | Days to 1000 mm³ MTV |
|---|---|---|---|---|---|---|---|---|
| A | 20% HPβCD | QW | IV | 1204.4 ± 177.8 | NA | NA | NA | 18.7 |
| B | I-263a 10 mg/kg | QW | IV | 706.9 ± 51.3 | 41.3 | 25.6 | <0.01 | 32.1 |
| C | I-263a 5 mg/kg | QW | IV | 759.3 ± 33.2 | 37 | 26.8 | <0.01 | 28.7 |
| D | Rituximab 5 mg/kg | QW | IV | 530.7 ± 85.4 | 55.9 | 46.8 | <0.001 | >77 |
| E | I-263a 10 mg/kg, Rituximab 5 mg/kg | QW, QW | IV, IV | 176.3 ± 88.8 | 85.4 | 114.6 | <0.001 | >120 |

TABLE 2a-continued

Combination of Compound I-263a and rituximab in the OCI-Ly10 xenograft model

| Study Group | Treatment | Dosing Regimen | Route | Tumor volume on Day 21 (±SEM) | TGI % | dAUC | P-value | Days to 1000 mm³ MTV |
|---|---|---|---|---|---|---|---|---|
| F | I-263a 5 mg/kg, Rituximab 5 mg/kg | QW, QW | IV, IV | 303.3 ± 107.2 | 74.8 | 79.4 | <0.001 | >120 |

TABLE 2b

Classification for in vivo combination of Compound I-263a and rituximab in the OCI-Ly10 xenograft model

| Treatment | Synergy score | SEM | P-value | Classification |
|---|---|---|---|---|
| I-263a 10 mg/kg, Rituximab 5 mg/kg | −42.1 | 14.9 | <0.05 | Synergy |

TABLE 2b-continued

Classification for in vivo combination of Compound I-263a and rituximab in the OCI-Ly10 xenograft model

| Treatment | Synergy score | SEM | P-value | Classification |
|---|---|---|---|---|
| I-263a 5 mg/kg, Rituximab 5 mg/kg | −4.1 | 17.8 | 0.821 | Additive |

Study 3: WSU-DLCL2 xenograft model

In the WSU-DLCL2 diffuse large B-cell lymphoma xenograft model, mice were inoculated, randomized on Day 0 (8 days post inoculation), and treatments began on Day 1 for all groups. Compound I-263a was tested at 5 mg/kg administered IV on a QW (once per week) schedule. Rituximab was tested at 5 mg/kg administered IV on a QW schedule. In the combination treatment group, Compound I-263a was administered first, followed immediately by the administration of rituximab. One group served as the vehicle-treated group (Group 1) receiving IV treatment with the vehicle for I-263a (20% HPβCD) on a QW schedule.

The combination arm of Compound I-263a at 5 mg/kg with rituximab at 5 mg/kg yielded additive effects during the 21-day treatment phase of the study. By Day 28 1/8 mice in the combination arm achieved complete regressions of the tumor. All single-agent I-263a treated mice were euthanized by Day 24 once the group sized reached 1000 mm³ or an individual tumor volume exceeded the humane end-point for size.

The treatment groups from Study 3 are shown in Table 3a. The combination effect for the treatment period is shown in Table 3b. Tumor growth curves are shown during the treatment period in FIG. 3.

TABLE 3a

Combination of Compound I-263a and rituximab in the WSU-DLCL2 xenograft model

| Study Group | Treatment | Dosing Regimen | Route | Tumor volume on Day 21 (±SEM) | TGI % | dAUC | P-value | Days to 1000 mm³ MTV |
|---|---|---|---|---|---|---|---|---|
| A | 20% HPβCD | QW | IV | 2147.2 ± 187.6 | NA | NA | NA | 9.5 |
| B | I-263a 5 mg/kg | QW | IV | 1340.3 ± 188.1 | 37.6 | 28.1 | <0.001 | 17.2 |
| C | Rituximab 5 mg/kg | QW | IV | 1097.5 ± 119.4 | 48.9 | 31.6 | <0.001 | 18.8 |
| D | I-263a 5 mg/kg, Rituximab 5 mg/kg | QW, QW | IV, IV | 665.1 ± 143.3 | 69.5 | 73.6 | <0.05 | 24.4 |

TABLE 3b

Classification for in vivo combination of Compound I-263a and rituximab in the WSU-DLCL2 xenograft model

| Treatment | Synergy score | SEM | P-value | Classification |
|---|---|---|---|---|
| I-263a 5 mg/kg, Rituximab 5 mg/kg | −11.0 | 19.5 | >0.05 | Additive |

Study 4: TMD8 Xenograft Model

In the TMD8 diffuse large B-cell lymphoma xenograft model, mice were inoculated, randomized on Day 0 (10 days post inoculation), and treatments began on Day 1 for all groups. Compound I-263a was tested at 25 mg/kg and 15 mg/kg administered IV on a QW (once per week) schedule. Rituximab was tested at 10 mg/kg administered IV on a QW schedule. In the combination treatment group, Compound I-263a was administered first, followed immediately by the administration of rituximab. One group served as the vehicle-treated group (Group 1) receiving IV treatment with the vehicle for I-263a (20% HPβCD) on a QW schedule.

The combination arm of Compound I-263a at either 25 mg/kg or 15 mg/kg with rituximab at 10 mg/kg yielded additive effects during the 18-day treatment phase of the study. By Day 120, 16/16 treated with I-263a at either dose plus Rituximab demonstrated complete tumor regressions. All single-agent I-263a treated mice were euthanized by Day 120 once the group sized reached 1000 mm³ or an individual tumor volume exceeded the humane end-point for size.

Figure 4A:
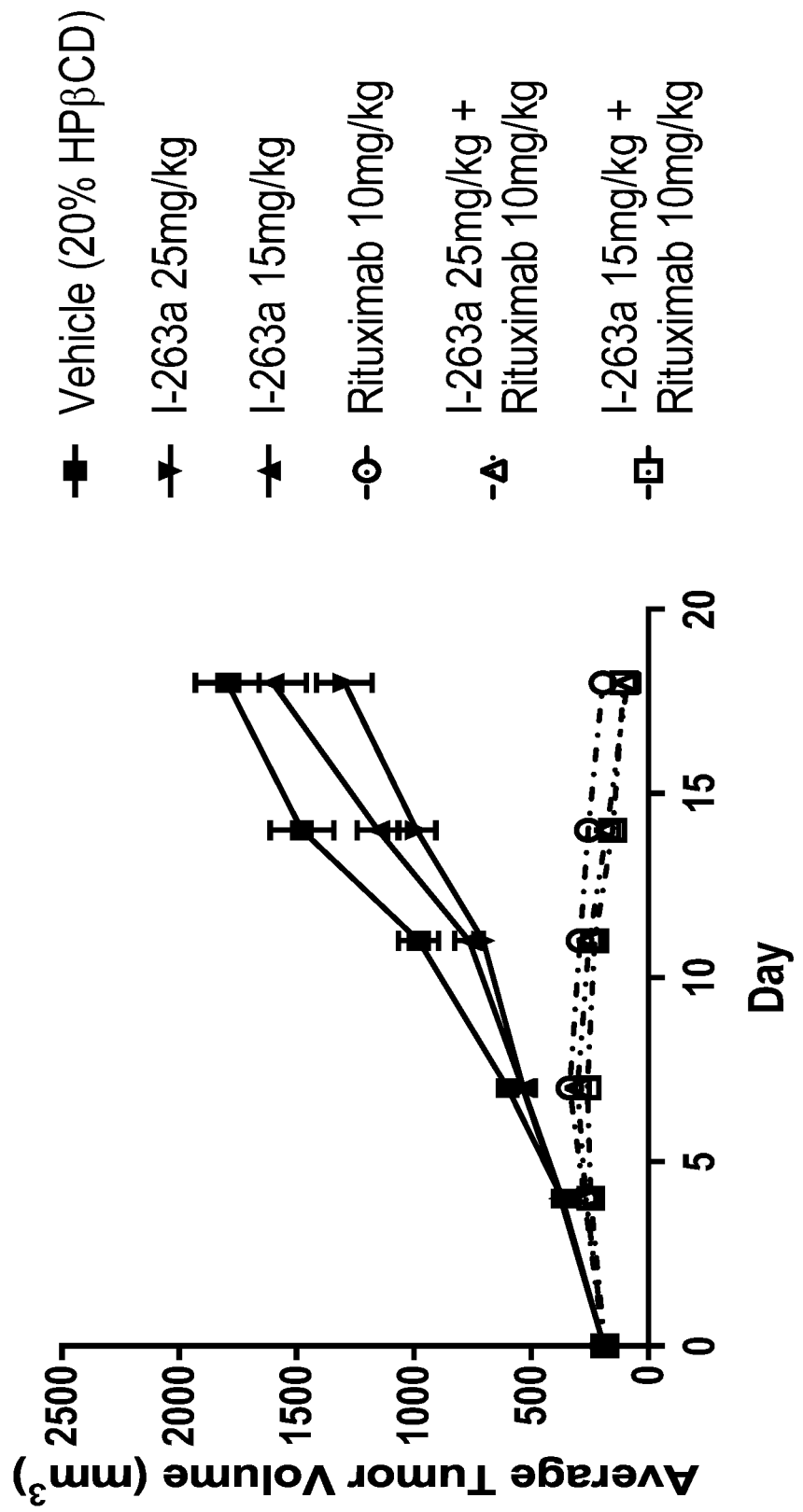
FIG. 4a shows a plot of tumor volume as a function of time during treatment period in a TMD8 xenograft model following administration of Compound I-263a and rituximab to mice.
Figure 4B:
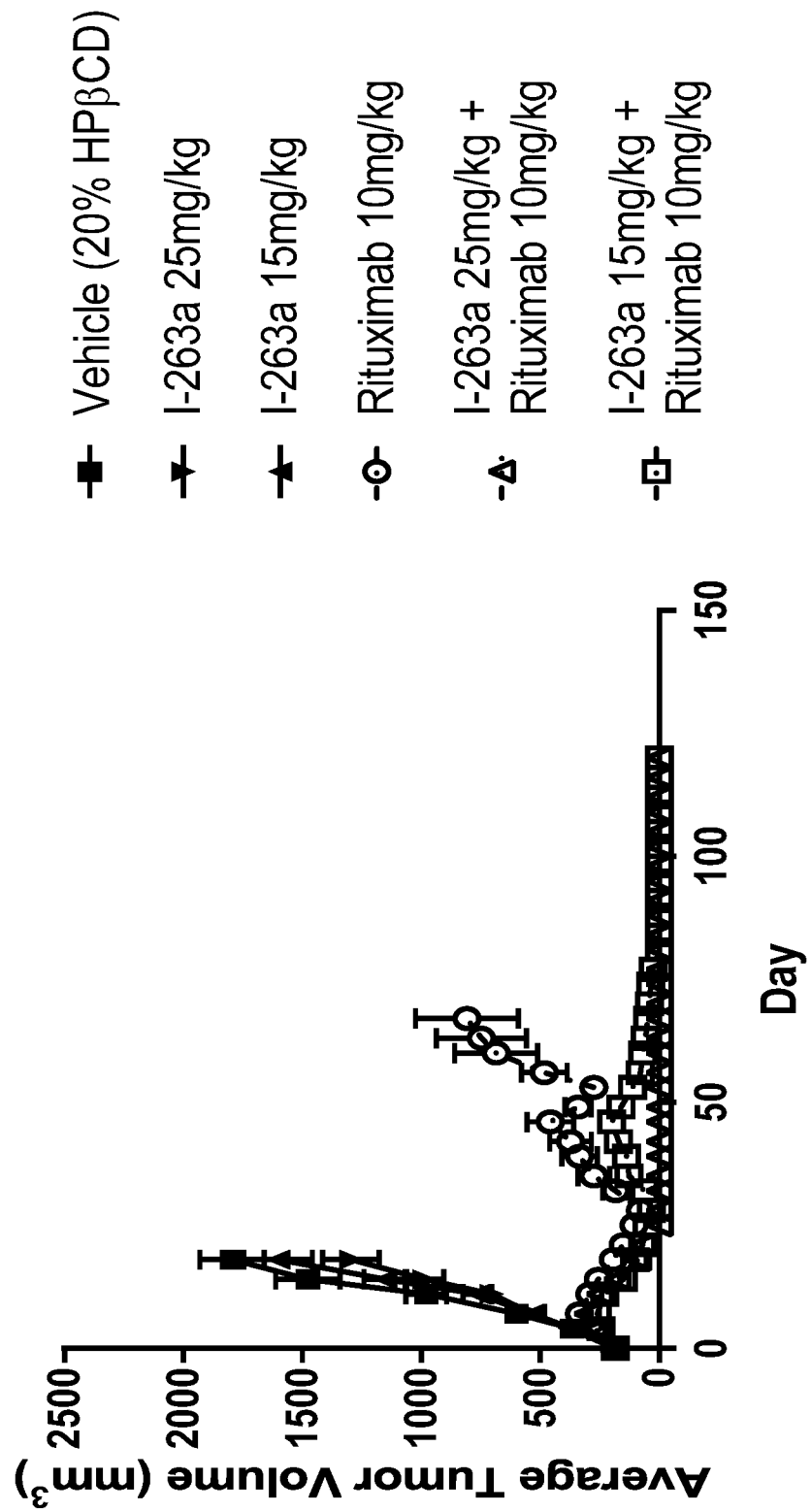
FIG. 4b shows a plot of tumor volume as a function of time during treatment and post-treatment periods in a TMD8 xenograft model following administration of Compound I-263a and rituximab to mice.

The treatment groups from Study 4 are shown in Table 4a. The combination effect for the treatment period is shown in Table 4b. Tumor growth curves are shown during the treatment period in FIG. 4a. Tumor growth curves for treatment and post-treatment periods are shown in FIG. 4b.

immediately by the administration of rituximab. One group served as the vehicle-treated group (Group 1) receiving IV treatment with the vehicle for I-263a (20% HPβCD) on a QW schedule.

The combination arm of Compound I-263a at 25 mg/kg with rituximab at 10 mg/kg yielded synergistic effects during the 11-day treatment phase of the study. The combination arm of Compound I-263a at 12.5 mg/kg with rituximab at 10 mg/kg yielded additive effects. Mice were continually monitored up to Day 147 post treatment initiation. Mice were euthanized when the average group tumor volume TABLE 4a Combination of Compound I-263a and rituximab in the TMD8 xenograft model

| Study Group | Treatment | Dosing Regimen | Route | Tumor volume on Day 18 (±SEM) | TGI % | dAUC | P-value | Days to 1000 mm³ MTV |
|---|---|---|---|---|---|---|---|---|
| A | 20% HPβCD | QW | IV | 1796 ± 136.6 | NA | NA | NA | 11.1 |
| B | I-263a 25 mg/kg | QW | IV | 1297.4 ± 120.2 | 27.8 | 13.6 | <0.05 | 14.1 |
| C | I-263a 15 mg/kg | QW | IV | 1604.1 ± 144.7 | 10.7 | 10.1 | <0.05 | 12.8 |
| D | Rituximab 10 mg/kg | QW | IV | 195 ± 40.5 | 89.1 | 81.8 | <0.001 | >67 |
| E | I-263a 25 mg/kg, Rituximab 10 mg/kg | QW, QW | IV, IV | 90 ± 5.9 | 95 | 92.0 | <0.001 | >120 |
| F | I-263a 15 mg/kg, Rituximab 10 mg/kg | QW, QW | IV, IV | 104 ± 6.2 | 94.2 | 97.1 | <0.001 | >120 |

TABLE 4b

Classification for in vivo combination of Compound I-263a and rituximab in the TMD8 xenograft model

| Treatment | Synergy score | SEM | P-value | Classification |
|---|---|---|---|---|
| I-263a 25 mg/kg, Rituximab 10 mg/kg | 5.4 | 10.5 | 0.613 | Additive |
| I-263a 15 mg/kg, Rituximab 10 mg/kg | −5.6 | 10.9 | 0.617 | Additive |

Study 5: PHTX-166L Xenograft Model

In the PHTX-166L patient-derived primary B-cell lymphoma xenograft model, mice were inoculated, randomized on Day 0 (24 days post inoculation), and treatments began on Day 1 for all groups. Compound I-263a was tested at 25 mg/kg and 12.5 mg/kg administered IV on a QW (once per week) schedule. Rituximab was tested at 10 mg/kg administered IV on a QW schedule. In the combination treatment group, Compound I-263a was administered first, followed exceeded 1000 mm³, when any individual mouse tumor volume exceeded the humane end-point for size, or when tumors began to ulcerate. On Day 147, 4/8 mice treated with Compound I-263a at 25 mg/kg plus rituximab at 10 mg/kg maintained complete tumor regression. 2/8 mice in this group were euthanized on Day 7 due to tumor ulceration. 1/8 mice in this group was euthanized on Day 49 due to ulceration. Combination treatment with Compound I-263a at 12.5 mg/kg plus rituximab at 10 mg/kg resulted in complete tumor regression in 1/8 mice on Day 47 (group euthanized on Day 47 due to large tumor volume or ulceration in remaining mice). All mice treated with single-agent Compound I-263a or rituximab were euthanized by Day 21 due to large tumor volume or ulceration.

Figure 5B:
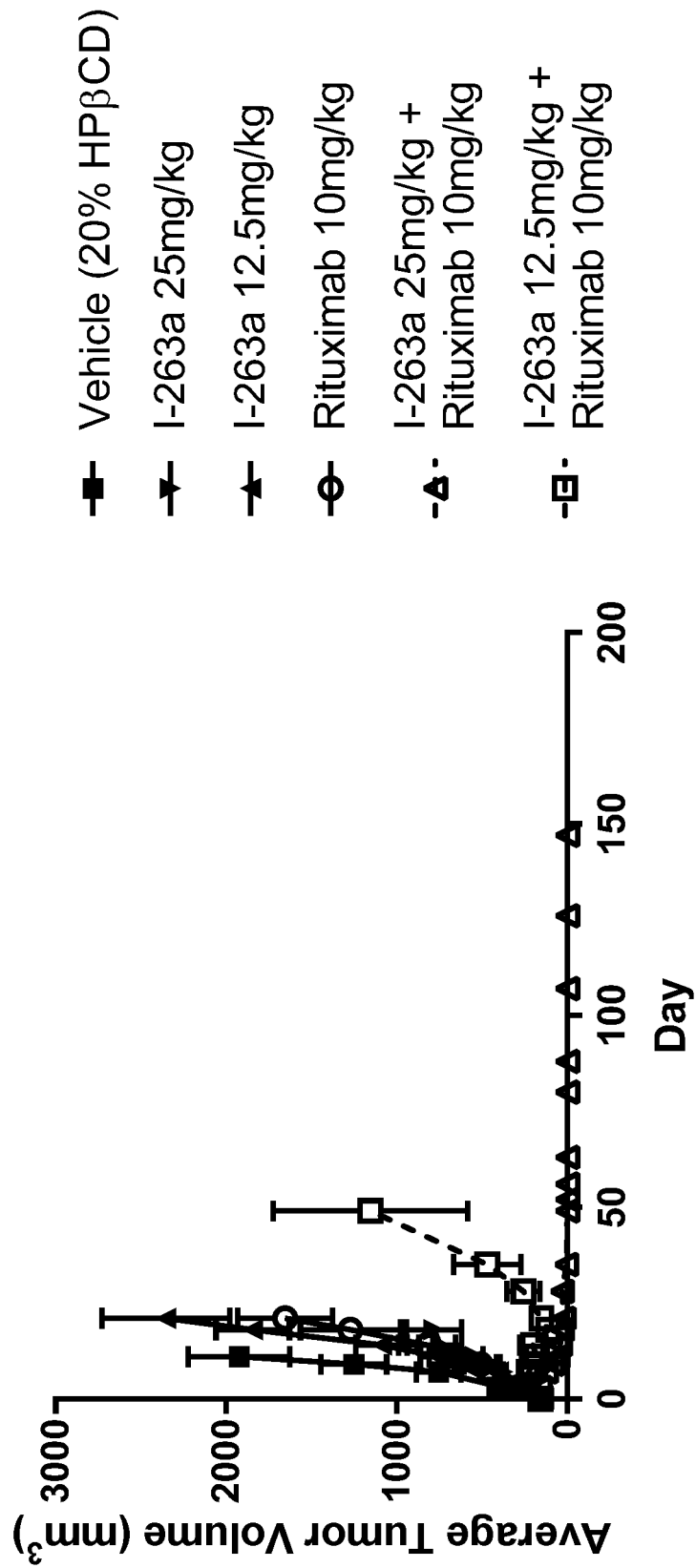
FIG. 5b shows a plot of tumor volume as a function of time during treatment and post-treatment periods in a PHTX-166L primary xenograft model following administration of Compound I-263a and rituximab to mice.

The treatment groups from Study 5 are shown in Table 5a. The combination effect for the treatment period is shown in Table 5b. Tumor growth curves are shown during the treatment period in FIG. 5a. Tumor growth curves for treatment and post-treatment periods are shown in FIG. 5b.

TABLE 5a

Combination of Compound I-263a and rituximab in the PHTX-166L xenograft model

| Study Group | Treatment | Dosing Regimen | Route | Tumor volume on Day 11 (±SEM) | TGI % | dAUC | P-value | Days to 1000 mm³ MTV |
|---|---|---|---|---|---|---|---|---|
| A | 20% HPβCD | QW | IV | 1926.1 ± 296.6 | 60.6 | NA | NA | 8 |

TABLE 5a-continued

Combination of Compound I-263a and rituximab in the PHTX-166L xenograft model

| Study Group | Treatment | Dosing Regimen | Route | Tumor volume on Day 11 (±SEM) | TGI % | dAUC | P-value | Days to 1000 mm³ MTV |
|---|---|---|---|---|---|---|---|---|
| B | I-263a 25 mg/kg | QW | IV | 540.2 ± 58.5 | 72 | 45.0 | <0.001 | >18 |
| C | I-263a 12.5 mg/kg | QW | IV | 758.2 ± 104.7 | 60.6 | 35.4 | <0.01 | 13.2 |
| D | Rituximab 10 mg/kg | QW | IV | 653.5 ± 158.5 | 66.1 | 38.3 | <0.01 | 15.6 |
| E | I-263a 25 mg/kg, Rituximab 10 mg/kg | QW, QW | IV, IV | 59.6 ± 14.9 | 96.9 | 123.9 | <0.001 | >147 |
| F | I-263a 12.5 mg/kg, Rituximab 10 mg/kg | QW, QW | IV, IV | 181.6 ± 55.2 | 90.6 | 84.3 | <0.001 | 45.8 |

TABLE 5b

Classification for in vivo combination of Compound I-263a and rituximab in the PHTX-166L xenograft model

| Treatment | Synergy score | SEM | P-value | Classification |
|---|---|---|---|---|
| I-263a 25 mg/kg, Rituximab 10 mg/kg | −35.1 | 12.3 | <0.05 | Synergy |
| I-263a 12.5 mg/kg, Rituximab 10 mg/kg | −10.4 | 11.9 | 0.397 | Additive |

Study 6: PHTX-166L Xenograft Model

In the PHTX-166L patient-derived primary B-cell lymphoma xenograft model, mice were inoculated, randomized on Day 0 (12 days post inoculation), and treatments began on Day 1 for all groups. Compound I-263a was tested at 5.0 mg/kg administered IV on a QW (once per week) schedule. Rituximab was tested at 5.0 mg/kg administered IV on a QW schedule. In the combination treatment group, Compound I-263a was administered first, followed immediately by the administration of rituximab. One group served as the vehicle-treated group (Group 1) receiving IV treatment with the vehicle for I-263a (20% HPβCD) on a QW schedule.

The combination arm of Compound I-263a at 5.0 mg/kg with rituximab at 5.0 mg/kg yielded synergistic effects during the 9-day treatment phase of the study. Mice were continually monitored up to Day 35 post treatment initiation. Mice were euthanized when the average group tumor volume exceeded 1000 mm³, when any individual mouse tumor volume exceeded the humane end-point for size, or when tumor began to ulcerate. On Day 35, 1/8 mice treated with I-263a plus rituximab had a complete tumor regression. All mice treated with single-agent Compound I-263a or rituximab were euthanized by Day 14 due to large tumor volume or ulceration.

Figure 6A:
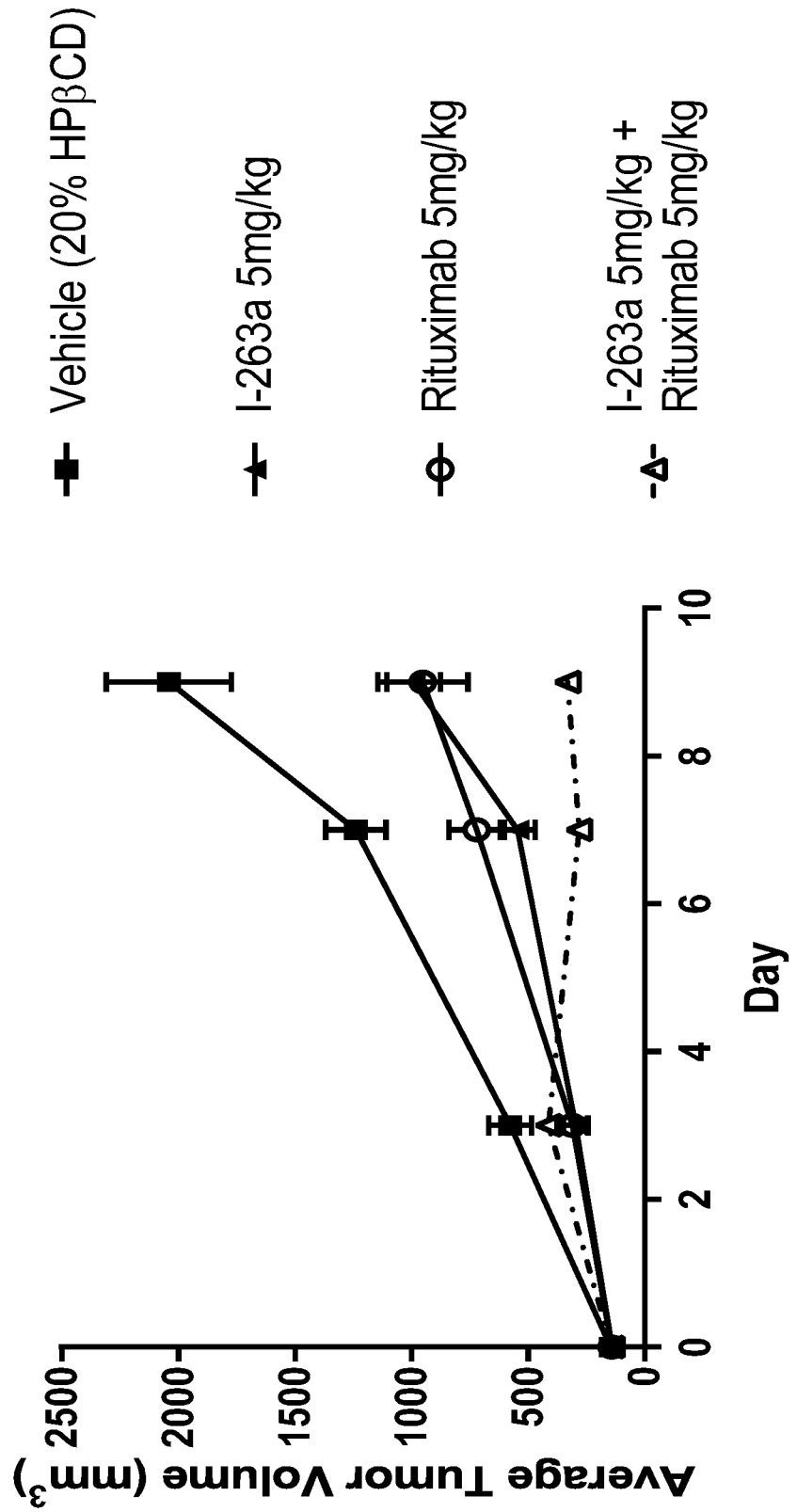
FIG. 6a shows a plot of tumor volume as a function of time during treatment period in a PHTX-166L primary xenograft model following administration of Compound I-263a and rituximab to mice.
Figure 6B:
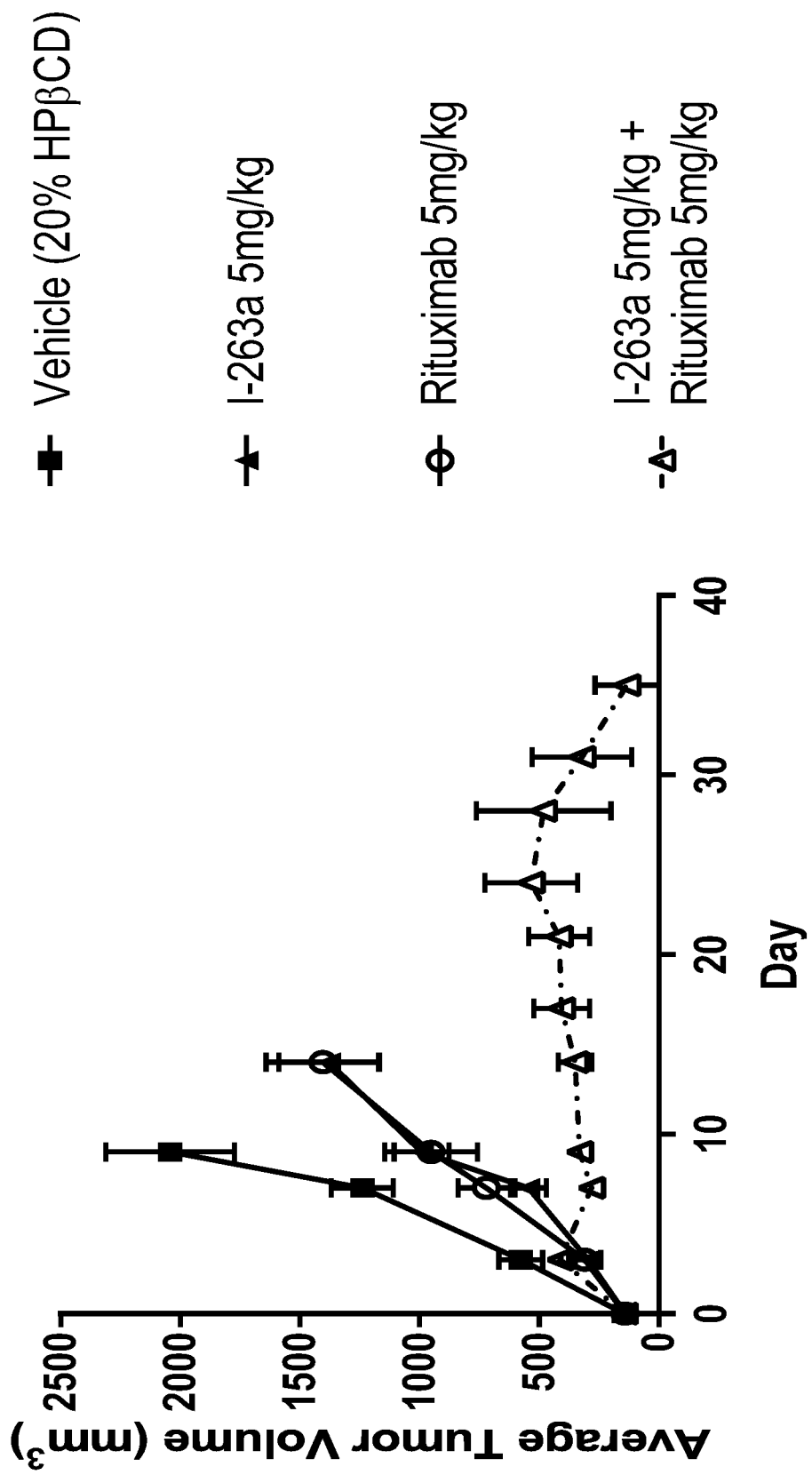
FIG. 6b shows a plot of tumor volume as a function of time during treatment and post-treatment periods in a PHTX-166L primary xenograft model following administration of Compound I-263a and rituximab to mice.

The treatment groups from Study 6 are shown in Table 6a. The combination effect for the treatment period is shown in Table 6b. Tumor growth curves are shown during the treatment period in FIG. 6a. Tumor growth curves for treatment and post-treatment periods are shown in FIG. 6b.

TABLE 6a

Combination of Compound I-263a and rituximab in the PHTX-166L xenograft model

| Study Group | Treatment | Dosing Regimen | Route | Tumor volume on Day 9 (±SEM) | TGI % | dAUC | P-value | Days to 1000 mm³ MTV |
|---|---|---|---|---|---|---|---|---|
| A | 20% HPβCD | QW | IV | 2042.2 ± 269.9 | NA | NA | NA | 5.6 |
| B | I-263a 5.0 mg/kg | QW | IV | 992.2 ± 115.2 | 51.4 | 34.3 | <0.001 | 9.1 |
| C | Rituximab 5.0 mg/kg | QW | IV | 953.3 ± 193.5 | 53.3 | 33.1 | <0.01 | 9.5 |
| D | I-263a 5.0 mg/kg, Rituximab 5.0 mg/kg | QW | IV | 331.9 ± 51.3 | 83.8 | 58.1 | <0.001 | >35 |

TABLE 6b

Classification for in vivo combination of Compound I-263a and rituximab in the PHTX-166L xenograft model

| Treatment | Synergy score | SEM | P-value | Classification |
|---|---|---|---|---|
| I-263a 5.0 mg/kg, Rituximab 5.0 mg/kg | 17.9 | 12.6 | 0.176 | Additive |

Example 2: Clinical Study Evaluating Compound I-263a in Combination with an Anti-CD20 Antibody in Treatment of Patients with Relapsed/Refractory CD20-Positive Non-Hodgkin Lymphoma A Phase 1b/2 clinical study will be conducted to evaluate the effects of a combination therapy, consisting of administration of a Rituximab intravenous infusion and of a Compound I-263a intravenous infusion, in adult patients with both CD20-positive (CD20+) and relapsed or refractory (r/r) non-Hodgkin lymphoma (NHL). The study will be conducted in 2 parts: 1) a phase 1b portion with dose escalation guided by Bayesian Logistic Regression Modeling (BLRM), open to patients with both indolent and aggressive CD20+ and r/r NHL; and 2) a phase 2 portion with two treatment arms (indolent CD20+ r/r NHL lymphoma and aggressive CD20+ r/r NHL in which mantle cell lymphoma inclusion is not permitted) conducted according to a Simon's two-stage optimal design.

The phase 1b portion will be a non-randomized dose-escalation study in patients with NHL to identify the maximum tolerated dose (MTD) and/or pharmacologically active dose (PAD) and schedule of the combination. The PAD is defined as the dose at which there is evidence of pharmacodynamic effects. PAD can be defined retrospectively once MTD is reached and it can be below MTD or coincide with it.

The phase 2 portion will be a non-randomized open label study with two parallel arms. During this phase, an evaluation of the antitumor efficacy of the combination at the dose selected at the end of phase 1b in patients with aggressive Non-Hodgkin Lymphoma (aNHL) and indolent non-Hodgkin lymphoma (iNHL) will be performed.

The starting dose of Compound I-263a will be 3 mg administrated intravenously. Compound I-263a will be administered as a 1-hour intravenous (IV) infusion on Days 1 and 8 in cycles of 21 days. Rituximab will be administered on a weekly schedule at 375 mg/m$^2$×3 doses followed by 375 mg/m$^2$ on Day 1 of subsequent 21-day cycles for both iNHL and aNHL patients, in cycles of 21 days. Rituximab and Compound I-263a will be administered intravenously until disease progression or unacceptable toxicity.

Dose escalation of Compound I-263a will be cohort-based with an adaptive design using BLRM with overdose control. The MTD (the highest dose of Compound I-263a in combination with rituximab for which the percentage of adverse events (AEs) meeting the dose limiting toxicity (DLT) definition at cycle 1 is <33%) will be selected. PAD, defined as the dose at which there is evidence of pharmacodynamic effects including the presence of small ubiquitin-like modifier [SUMO]-Compound I-263a adducts, reduction in small ubiquitin-like modifier 2/small ubiquitin-like modifier 3 conjugates, induction of a type 1 interferon signature in blood (e.g., increase in cytokines/chemokines involved in type 1 interferon signaling) will be identified. The recommended phase 2 dose for the Compound I-263a/rituximab combination will be determined after considering all available safety data, pharmacokinetic (PK) data, pharmacodynamic information, and after any early antitumor activity is observed.

Toxicity will be evaluated according to the National Cancer Institute Common Terminology Criteria for Adverse Events, version 5.0.

Dose escalation decisions will be made by the clinical study team (CST) based on the DLTs meeting the criteria above that occur during the first three weeks of treatment for each patient. Treatment-emergent adverse events (TEAEs) meeting DLT definitions occurring in later cycles will determine the suitability of the MTD as the recommended phase 2 dose.

Intrapatient dose escalation will be permitted only when patients in the next dose level (DL) cohort have completed assessment for Cycle 1 and a decision has been made that this DL does not exceed the MTD.

Every patient must be hospitalized for drug administration and observation (for a minimum of 18 hours after the end of Compound I-263a infusion) for the first infusion Cycle 1, Day 1 (C1D1) of Compound I-263a in combination with rituximab during dose escalation. Hospitalization is not required after the first 3 patients at a DL or expansion of previously cleared DL, and only if the risk of infusion reactions is considered low based on previous experience. If Grade 3 or greater infusion-related reaction (IRR) or cytokine release syndrome (CRS) are not observed at PAD or MTD, or if the safety data from the ongoing first-in-human TAK-981-1002 study (Clinical Trial.gov Identification No: NCT03648372) support the removal of the requirement of hospitalization for the first dose of Compound I-263a, this will be considered by the CST.

Patient enrollment will be staggered between the first and second patients by 1 week during dose escalation at all DLs. At each DL, the second and third patients can be dosed concurrently if the first patient in the cohort has gone through the Day 8 visit without clinically significant acute toxicities. If more than 3 patients are to be enrolled in a DL or if de-escalation is indicated, staggering will not be required unless indicated by safety findings.

Once the phase 1b dose-escalation portion of the study is completed and the MTD and/or PAD determined, the CST will open the phase 2 part of the study. If infusion reactions or CRS of Grade 2 or greater is not observed at PAD or MTD, the requirement of hospitalization for the first dose will be removed for the phase 2 study.

This study will enroll up to approximately 90 subjects.

Phase 1b Primary Endpoints

The primary endpoints for the phase 1b trial may include Frequency of TEAEs overall and per DL; Number of patients with DLTs per DL; Number/percentage of patients with ≥Grade 3 TEAEs; Number/percentage of patients with 1 or more serious adverse events; Number/percentage of patients with 1 or more TEAEs leading to dose modifications (delay, interruption or reduction) and treatment discontinuations; Number/percentage of patients with clinically significant laboratory values; and Number/percentage of patients with clinically significant vital sign measurements.

Phase 2 Endpoints

The primary endpoints for the phase 2 trial will include: Overall response rate (ORR) (complete response+partial response) as defined by the investigator according to Lugano Classification for lymphomas.

The trial will be conducted in conformance with Good Clinical Practices.

What is claimed is:

1. A method of treating a disorder, wherein the disorder is lymphoma or leukemia, comprising administering to a patient in need of said treating a combination of [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, and an anti-CD20 antibody.

2. The method of claim 1, wherein the anti-CD20 antibody is a Type I anti-CD20 antibody.

3. The method of claim 1, wherein the anti-CD20 antibody is selected from the group consisting of ublituximab, ofatumumab, ocrelizumab, veltuzumab, obinutuzumab, AME-133v, ocaratuzumab, PRO131921, tositumomab, ibritumomab-tiuxetan, hA20, BLX-301, Reditux, PRO70769, and rituximab.

4. The method of claim 1, wherein the anti-CD20 antibody is rituximab.

5. The method of claim 1, wherein the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, is administered orally, intravenously, or subcutaneously.

6. The method of claim 1, wherein the [(1R,2S,4R)-4-{[5-({4-[(1R)-7-chloro-1,2,3,4-tetrahydroisoquinolin-1-yl]-5-methyl-2-thienyl}carbonyl) pyrimidin-4-yl]amino}-2-hydroxycyclopentyl]methyl sulfamate (Compound I-263a) or a pharmaceutically acceptable salt thereof, is administered by intravenous infusion.

7. The method of claim 1, wherein the disorder is CD20 positive chronic lymphocytic leukemia or CD20 positive non-Hodgkin's lymphoma.

8. The method of claim 1, wherein the disorder is follicular lymphoma (FL), marginal zone lymphoma (MZL), mantle cell lymphoma (MCL), Diffuse large B-cell lymphoma (DLBCL), or Burkitt lymphoma.

9. The method of claim 1, wherein the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, is administered once every two weeks, once every week, twice a week, three times a week, or daily.

10. The method of claim 1, wherein the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, is administered on days 1 and 8 of a 21 day cycle or on days 1, 4, 8, and 11 of a 21 day cycle.

11. The method of claim 1, wherein the anti-CD20 antibody is administered once every two weeks, once every week, twice a week, three times a week, or daily.

12. The method of claim 11, wherein the anti-CD20 antibody is administered once every week.

13. The method of claim 1, wherein the anti-CD20 antibody is administered on Day 1 of a treatment cycle.

14. The method of claim 13, wherein the treatment cycle is 21 days or 28 days.

15. The method of claim 1, wherein the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, and the anti-CD20 antibody are administered simultaneously once every eight weeks, once every four weeks, once every two weeks, once every week, twice a week, three times a week, daily, on days 1 and 8 of a 21 day cycle, or on days 1, 4, 8, and 11 of a 21 day cycle.

16. The method of claim 1, wherein:
the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, is administered orally once every two weeks, once every week, twice a week, three times a week, daily, on days 1 and 8 of a 21 day cycle, or on days 1, 4, 8, and 11 of a 21 day cycle; and
the anti-CD20 antibody is separately administered once every eight weeks, once every four weeks, once every two weeks, once every week, twice a week, three times a week, daily, on day 1 of a 21 day cycle, or once every week for three doses followed by administration on day 1 of one or more subsequent 21 day cycles.

17. The method of claim 1, wherein the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, is administered on days 1, 4, 8, and 11 of a 21 day cycle.

18. The method of claim 9, wherein the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a), or a pharmaceutically acceptable salt thereof, is administered once every week.

19. The method of claim 18, wherein the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, is administered in an amount of 60 mg on each day of dosing.

20. The method of claim 18, wherein the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, is administered in an amount of 120 mg on each day of dosing.

21. The method of claim 1, wherein:
the anti-CD20 antibody is rituximab;
the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, is administered in an amount of 60 mg or 120 mg on each day of dosing;
the rituximab is administered in an amount of 375 $mg/m^2$ on each day of dosing; and
the [(1R,2S,4R)-4-{[5-({4-[(1R)-7-chloro-1,2,3,4-tetrahydroisoquinolin-1-yl]-5-methyl-2-thienyl}carbonyl)pyrimidin-4-yl]amino}-2-hydroxycyclopentyl]methyl sulfamate (Compound I-263a) or a pharmaceutically acceptable salt thereof, is administered once every week for one or more treatment cycles.

* * * * *